United States Patent
Coleman et al.

(10) Patent No.: US 9,757,484 B2
(45) Date of Patent: *Sep. 12, 2017

(54) STERILIZATION OF CIPROFLOXACIN COMPOSITION

(71) Applicant: Otonomy, Inc., San Diego, CA (US)

(72) Inventors: Scott H. Coleman, San Diego, CA (US); Wei-Cheng Liaw, San Diego, CA (US); Jerry Wroblewski, San Mateo, CA (US); Robert Savel, San Diego, CA (US)

(73) Assignee: OTONOMY, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/928,920

(22) Filed: Oct. 30, 2015

(65) Prior Publication Data

US 2016/0279274 A1    Sep. 29, 2016

Related U.S. Application Data

(63) Continuation of application No. 14/789,771, filed on Jul. 1, 2015, now Pat. No. 9,220,796.

(60) Provisional application No. 62/020,940, filed on Jul. 3, 2014.

(51) Int. Cl.

| | | |
|---|---|---|
| *A61K 9/14* | (2006.01) | |
| *A61K 9/16* | (2006.01) | |
| *A61K 31/47* | (2006.01) | |
| *A61K 31/445* | (2006.01) | |
| *A61L 2/00* | (2006.01) | |
| *A61K 9/00* | (2006.01) | |
| *A61K 31/496* | (2006.01) | |
| *A61K 47/10* | (2017.01) | |
| *A61K 9/06* | (2006.01) | |

(52) U.S. Cl.
CPC .......... *A61L 2/0023* (2013.01); *A61K 9/0046* (2013.01); *A61K 9/06* (2013.01); *A61K 31/496* (2013.01); *A61K 47/10* (2013.01); *A61L 2/0017* (2013.01); *A61L 2/0029* (2013.01)

(58) Field of Classification Search
None
See application file for complete search history.

(56) References Cited

U.S. PATENT DOCUMENTS

| | | |
|---|---|---|
| 4,938,763 A | 7/1990 | Dunn et al. |
| 5,033,252 A | 7/1991 | Carter |
| 5,052,558 A | 10/1991 | Carter |
| 5,323,907 A | 6/1994 | Kalvelage |
| 5,324,519 A | 6/1994 | Dunn et al. |
| 5,421,818 A | 6/1995 | Arenberg |
| 5,474,529 A | 12/1995 | Arenberg |
| 5,476,446 A | 12/1995 | Arenburg |
| 5,702,716 A | 12/1997 | Dunn et al. |
| 5,744,153 A | 4/1998 | Yewey et al. |
| 5,861,174 A | 1/1999 | Stratton et al. |
| 5,990,194 A | 11/1999 | Dunn et al. |
| 6,004,573 A | 12/1999 | Rathi et al. |
| 6,045,528 A | 4/2000 | Arenberg et al. |
| 6,066,292 A | 5/2000 | Purwar |
| 6,117,949 A | 9/2000 | Rathi et al. |
| 6,139,870 A | 10/2000 | Verrecchia |
| 6,201,072 B1 | 3/2001 | Rathi et al. |
| 6,287,588 B1 | 9/2001 | Shih et al. |
| 6,589,549 B2 | 7/2003 | Shih et al. |
| 7,018,645 B1 | 3/2006 | Piao et al. |
| 9,220,796 B1 * | 12/2015 | Coleman ................. A61K 9/06 |
| 2006/0034889 A1 | 2/2006 | Jo et al. |
| 2007/0110788 A1 | 5/2007 | Hissong et al. |
| 2007/0167918 A1 | 7/2007 | Reed et al. |
| 2012/0277199 A1 | 11/2012 | Ye et al. |

FOREIGN PATENT DOCUMENTS

| | | |
|---|---|---|
| AU | 2014200457 A1 | 2/2014 |
| WO | WO-9932156 A2 | 7/1999 |
| WO | WO-03026671 A1 | 4/2003 |
| WO | WO-2010011609 A2 | 1/2010 |
| WO | WO-2011049960 A2 | 4/2011 |
| WO | WO-2015031393 A1 | 3/2015 |

OTHER PUBLICATIONS

Chen et al. Design and preparation of thermosensitive in situ gel of dexamethasone sodium phosphate. J Guangdong Coll Pharm 23(5):518-521 (2007) (English abstract).

Chen et al. Evaluation of thermosensitive in situ gel using dynamic rheological experiment. Chin Pharm J 43(6):444-447 (2008) (English abstract).

Chen et al. In vivo Distribution and Pharmacokinetics of Dexamethasone Acetate Nanoparticles Thermosensitive in situ Gel Following Intratympanic Injection. Chin. J. Otorhinolaryngol Head Neck Surg 42:533-534 (2007).

Chen et al. In vivo distribution and pharmacokinetics of dexamethasone sodium phosphate thermosensitive in situ gel following intratympanic injection. Sichuan Da Xue Xue Bao Yi Xue Ban 37(3):456-459 (2006) (English translation).

(Continued)

*Primary Examiner* — Jeffrey T Palenik
(74) *Attorney, Agent, or Firm* — Wilson Sonsini Goodrich & Rosati

(57) ABSTRACT

Disclosed herein are methods of making sterilized ciprofloxacin compositions. In some embodiments, the method includes the steps of: (a) forming an aqueous suspension comprising ciprofloxacin particles; (b) heating the aqueous suspension comprising ciprofloxacin particles at a temperature range of from about 100° C. to about 120° C.; and (c) allowing the aqueous suspension comprising ciprofloxacin particles to cool down. Also described herein are otic formulations containing ciprofloxacin formed by the disclosed methods, and therapeutic use of such otic formulation for providing sustained release of ciprofloxacin into the ear for treating various otic disorders and conditions.

20 Claims, 5 Drawing Sheets

(56) References Cited

OTHER PUBLICATIONS

Chen et al. Preliminary study on brain-targeted drug delivery via inner ear. Acta Pharmaceutica Sinica 42:1102-1106 (2007) (English Abstract).
Chen et al. Preparation and characterization of dexamethasone acetate-loaded solid lipid nanoparticles. Chinese J Pharm 39(4):261-264 (2008) (English abstract).
Chen et al. Study on dexamethasone thermosensitive in situ gel for treating deafness. Chin Pharm J 41(9):685-688 (2006) (English abstract).
Feng et al. Effect of Poloxamer 407 on the cochlear orphology and hearing function after perfusion in round window: experiment with guinea pigs. National Medical Journal of China 87:2289-2291 (2007) (English Translation).
Jeong et al. Biodegradable block copolymers as injectable drug-delivery systems. Nature 388:860-862 (1997).
Jeong et al. Drug release from biodegradable injectable thermosensitive hydrogel of PEG-PLGA-PEG triblock copolymers. Journal of Controlled Release 63:155-163 (2000).
Jeong et al. Thermosensitive sol-gel reversible hydrogels. Advanced Drug Delivery Reviews 54:37-51 (2002).
Microbiological Evaluation of Filters for Sterilizing Liquids. Washington, D.C: Health Industry Manufacturers Association HIMA Doc. No. 3, vol. 4 (1981).
Pappas et al. Topical Antibiotic Ear Drops: Are They Safe? Int J Clin Pract. 60:1115-1119 (2006).
PCT/US2015/038872 International Search Report and Written Opinion dated Sep. 30, 2015.
Richard et al. Effects of sterilizing-grade filters on the physico-chemical properties of onion-like vesicles. International Journal of Pharmaceutics 312(1-2):144-150 (2006).
Ross et al. Aqueous Solubilities of some variously Substituted Quinolone Antimicrobials. Int'l J of Pharm 63:237-250 (1990).
SciFinder NPL Search Results; downloaded Aug. 28, 2015.
Taktak et al. Assay of Pyrogens by Interleukin-6 Release from Monocytic Cell Lines. J. Pharm. Pharmacol. 43:578-582 (1991).
The U. S. Food and Drug Administration has provided regulatory guidance in the publication: Guidance for Industry: Sterile Drug Products Produced by Aseptic Processing. available at: <ahref="http://www.fda.gov/cder/guidance/5882fn1.htm"http://www.fda.gov/cder/guidance/5882fn1.htm/a> (Aug. 2003).
Viegas et al. Osmotic behavior of poloxamer 407 and other non-ionic surfactants in aqueous solutions. Int. J. Pharm. 160:157-162 (1998).

\* cited by examiner

STERILIZATION OF CIPROFLOXACIN COMPOSITION

CROSS-REFERENCE

This application is a continuation application of U.S. patent application Ser. No. 14/789,771, filed Jul. 1, 2015, which claims the benefit of U.S. Provisional Application No. 62/020,940, filed Jul. 3, 2014, which application is incorporated herein by reference in its entirety.

BACKGROUND OF THE INVENTION

Ciprofloxacin is a quinolone compound with antimicrobial activities. Some ciprofloxacin-containing pharmaceutical compositions require sterility for specific medical applications.

SUMMARY OF THE INVENTION

Described herein are methods of making sterilized ciprofloxacin compositions. In some embodiments, the method includes the steps of: (a) forming an aqueous suspension comprising ciprofloxacin particles; (b) heating the aqueous suspension comprising ciprofloxacin particles at a temperature range of from about 100° C. to about 120° C.; and (c) allowing the aqueous suspension comprising ciprofloxacin particles to cool down.

In some embodiments, the aqueous suspension in step (a) is formed by mixing ciprofloxacin particles with water. In some embodiments, the aqueous suspension in step (a) is formed by homogenizing ciprofloxacin particles in water.

In some embodiments, the aqueous suspension in step (a) is essentially free of organic solvent.

In some embodiments, the ciprofloxacin particles in step (a) are in the form of ciprofloxacin anhydrous particles, ciprofloxacin hydrate particles, or a combination thereof. In some embodiments, the ciprofloxacin particles in step (a) are essentially in the form of ciprofloxacin hydrate particles.

In some embodiments, the ciprofloxacin particles in step (a) are present in the aqueous suspension at a concentration of from about 4 wt % to about 30 wt %. In some embodiments, the ciprofloxacin particles in step (a) are present in the aqueous suspension at a concentration of from about 4 wt % to about 20 wt %. In some embodiments, the ciprofloxacin particles in step (a) are present in the aqueous suspension at a concentration of from about 4 wt % to about 16 wt %.

In some embodiments, the ciprofloxacin particles in step (a) have a D90 of from about 40 µm to about 80 µm. In some embodiments, the ciprofloxacin particles in step (a) have a D90 of from about 45 µm to about 75 µm. In some embodiments, the ciprofloxacin particles in step (a) have a D90 of from about 50 µm to about 70 µm. In some embodiments, the ciprofloxacin particles in step (a) have a D90 of from about 40 µm to about 80 µm.

In some embodiments, the aqueous suspension in step (b) is heated at a temperature of from about 101° C. to about 119° C. In some embodiments, the aqueous suspension in step (b) is heated at a temperature of from about 102° C. to about 118° C. In some embodiments, the aqueous suspension in step (b) is heated at a temperature of from about 103° C. to about 117° C. In some embodiments, the aqueous suspension in step (b) is heated at a temperature of from about 104° C. to about 116° C. In some embodiments, the aqueous suspension in step (b) is heated at a temperature of from about 105° C. to about 115° C.

In some embodiments, the aqueous suspension in step (b) is heated for a period of from about 30 minutes to about 5 hours. In some embodiments, the aqueous suspension in step (b) is heated for a period of from about 40 minutes to about 4 hours. In some embodiments, the aqueous suspension in step (b) is heated for a period of from about 50 minutes to about 3 hours. In some embodiments, the aqueous suspension in step (b) is heated for a period of from about 1 hour to about 2 hours.

In some embodiments, the aqueous suspension in step (b) is heated at a temperature of about 115° C. for a period of about 1 hour. In some embodiments, the aqueous suspension in step (b) is heated at a temperature of about 105° C. for a period of about 2 hour. In some embodiments, the aqueous suspension in step (b) is heated at a temperature of about 110° C. for a period of from about 1 hour to about 2 hours.

In some embodiments, the aqueous suspension in step (b) is heated at a constant temperature within the temperature range. In some embodiments, the aqueous suspension in step (b) is heated at variable temperatures within the temperature range.

In some embodiments, the ciprofloxacin particles in step (b) are homogenized in the aqueous suspension when heated.

In some embodiments, the ciprofloxacin particles in step (c) are essentially in the form of ciprofloxacin hydrate particles.

In some embodiments, the ciprofloxacin particles in step (c) are homogenized in the aqueous suspension during cooling. In some embodiments, the aqueous suspension in step (c) is allowed to cool down to from about 2° C. to about 10° C.

In some embodiments, the ciprofloxacin particles in step (c) have a D90 of from about 5 µm to about 40 µm after cooling down. In some embodiments, the ciprofloxacin particles in step (c) have a D90 of from about 10 µm to about 35 µm after cooling down. In some embodiments, the ciprofloxacin particles in step (c) have a D90 of from about 15 µm to about 25 µm after cooling down.

In some embodiments, the methods of making sterilized ciprofloxacin compositions further include the step of: (d) combining the cooled aqueous suspension comprising ciprofloxacin particles with a sterilized aqueous solution comprising a thermoreversible polymer to form an otic formulation.

In some embodiments, the thermoreversible polymer is a polyoxyethylene-polyoxypropylene triblock copolymer. In some embodiments, the thermoreversible polymer is poloxamer 407.

In some embodiments, the aqueous solution further comprises a buffer agent. In some embodiments, the buffer agent is tromethamine.

In some embodiments, the aqueous solution further comprises a pH adjusting agent in an amount to adjust the pH of the aqueous solution to from about 7.0 to about 8.0. In some embodiments, the pH adjusting agent is hydrochloric acid.

In some embodiments, the aqueous solution further comprises an osmolarity modifier. In some embodiments, the osmolarity modifier is sodium chloride.

In some embodiments, the aqueous solution is sterilized through filtration sterilization, heat sterilization, or radiation sterilization. In some embodiments, the aqueous solution is sterilized through filtration sterilization. In some embodiments, the aqueous solution is sterilized by passing through a cold sterilization filter.

In some embodiments, the aqueous solution is allowed to cool down to from about 2° C. to about 10° C.

In some embodiments, the aqueous suspension and the aqueous solution are combined under aseptic condition.

In some embodiments, the otic formulation comprises from about 5 wt % to about 7 wt % of ciprofloxacin. In some embodiments, the otic formulation comprises from about 5.5 wt % to about 6.5 wt % of ciprofloxacin. In some embodiments, the otic formulation comprises from about 1.5 to about 2.5 wt % of ciprofloxacin.

In some embodiments, the otic formulation comprises from about 14 wt % to about 19 wt % of the thermoreversible polymer. In some embodiments, the otic formulation comprises from about 15 wt % to about 17 wt % of the thermoreversible polymer. In some embodiments, the otic formulation comprises from about 15.5 wt % to about 16.5 wt % of the thermoreversible polymer.

In some embodiments, the otic formulation has a pH of from about 7.0 to about 8.0.

In some embodiments, the otic formulation has an osmolarity of from about 270 mOsm/L to about 320 mOsm/L.

In some embodiments, the otic formulation has less than about 50 colony forming units (cfu) of microbiological agents per gram of formulation.

In some embodiments, the otic formulation has less than about 5 endotoxin units (EU) per kg of body weight of a subject.

In some embodiments, the otic formulation has a gelation temperature between about 19° C. to about 42° C.

Also described herein are otic formulations containing ciprofloxacin formed by the disclosed methods, and therapeutic use of such otic formulation for providing sustained release of ciprofloxacin into the ear for treating various otic disorders and conditions.

In some embodiment, the sterilized otic formulation comprising: from about from 4.5 wt % to 6 wt % multiparticulate ciprofloxacin; from 14 wt % to 16 wt % poloxamer; and water, wherein the composition has a pH of 7.0-7.8, an osmolarity of 270-320 mOsm/L, and a gelation temperature of 20-30° C., and wherein the composition provides sustained release of a therapeutically effective amount of ciprofloxacin into the ear for a period of at least 5 days after a single administration. In some embodiment, the sterilized otic formulation comprising: from about from 1.5 wt % to 2.5 wt % multiparticulate ciprofloxacin; from 14 wt % to 16 wt % poloxamer; and water, wherein the composition has a pH of 7.0-7.8, an osmolarity of 270-320 mOsm/L, and a gelation temperature of 20-30° C., and wherein the composition provides sustained release of a therapeutically effective amount of ciprofloxacin into the ear for a period of at least 5 days after a single administration.

In some embodiments, the multiparticulate ciprofloxacin is micronized ciprofloxacin. In some embodiments, the micronized ciprofloxacin has a D90 of from about 5 µm to about 40 µm. In some embodiments, the micronized ciprofloxacin has a D90 of from about 10 µm to about 35 µm. In some embodiments, the micronized ciprofloxacin has a D90 of from about 15 µm to about 25 µm.

In some embodiments, the poloxamer is poloxamer 407.

In some embodiments, the otic formulation further comprises tromethamine.

In some embodiments, the otic formulation further comprises a sodium salt for osmolarity adjustment.

In some embodiments, the composition provides sustained release of a therapeutically effective amount of ciprofloxacin into the ear for a period of at least 10 days after a single administration.

In some embodiments, the composition provides sustained release of a therapeutically effective amount of ciprofloxacin into the ear for a period of at least 14 days after a single administration.

In some embodiments, the composition has less than 5 endotoxin units (EU) per kg of body weight. In some embodiments, the ciprofloxacin is moist-heat sterilized.

In some embodiments, the ciprofloxacin is moist-heat sterilized and the poloxamer is filtration sterilized.

Also disclosed herein is a ready-to-use otic product, comprising an aseptic vial and a sterilized otic formulation as described herein.

DETAILED DESCRIPTION OF THE INVENTION

Figure 1:
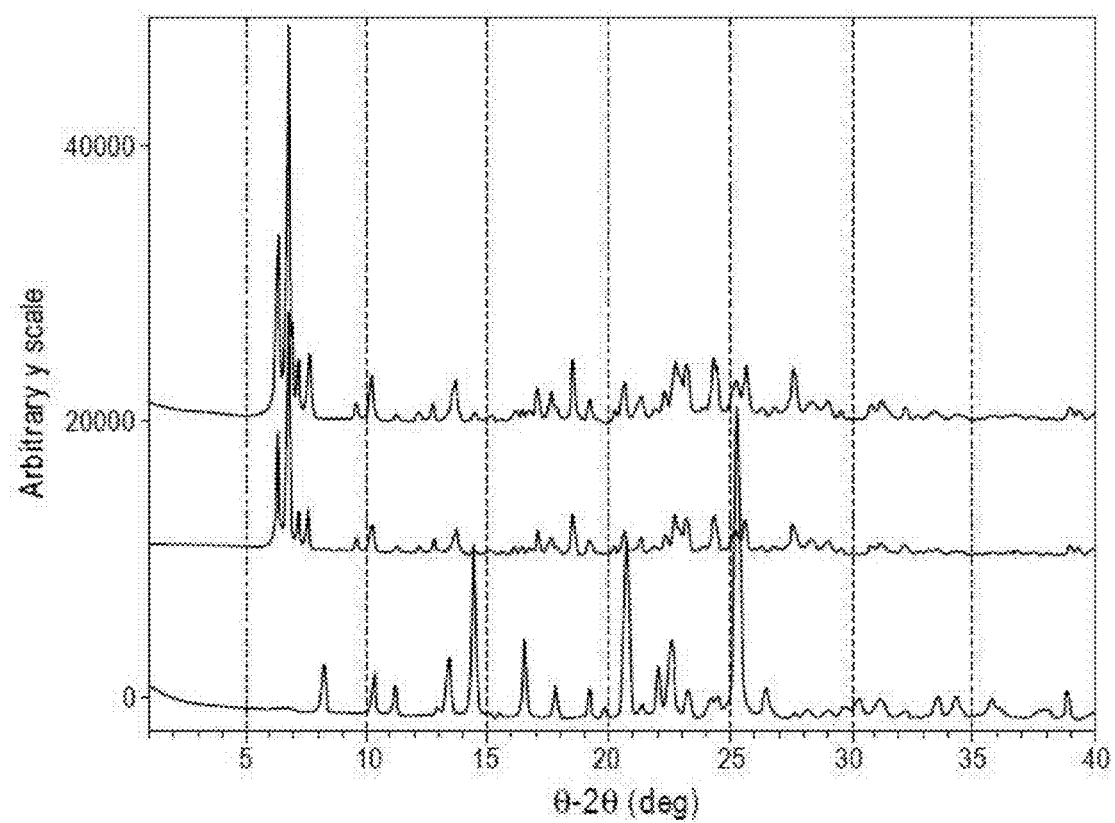
FIG. 1 shows X-ray characterization of ciprofloxacin anhydrous, ciprofloxacin hydrate, and an aqueous ciprofloxacin suspension formed according to the method disclosure herein.

Provided herein are methods of making sterilized ciprofloxacin compositions. Also described herein are otic formulations containing ciprofloxacin formed by the disclosed methods, and therapeutic use of such otic formulation for providing sustained release of ciprofloxacin into the ear for treating various otic disorders and conditions.

Sterilization of Pharmaceutical Products

Pharmaceutical compositions sometimes need to be sterilized for specific medical or therapeutic applications. The goal is to provide a safe pharmaceutical product, relatively free of infection causing micro-organisms. The U. S. Food and Drug Administration has provided regulatory guidance in the publication "Guidance for Industry: Sterile Drug Products Produced by Aseptic Processing" available at: http://www.fda.gov/cder/guidance/5882fnl.htm, which is incorporated herein by reference in its entirety.

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation or E-beam irradiation. In some embodiment, a process for the preparation of an otic therapeutic formulation comprises subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In some embodiments, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process. For example, a typical moist heat sterilization process, heating to 121.5 degrees Celsius and holding for a certain duration is often used to sterilize liquid formulations and this method is often regarded by regulatory agencies as acceptable for ensuring sterility.

Dry heat sterilization is a method which is used to kill microorganisms and perform depyrogenation at elevated temperatures. This process takes place in an apparatus suitable for heating HEPA-filtered microorganism-free air to temperatures of for example 130-180° C. for the sterilization process and to temperatures of for example 230-250° C. for the depyrogenation process. Water to reconstitute concentrated or powdered formulations is also sterilized by autoclave.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 μm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3, Washington, D.C.: Health Industry Manufacturers Association, 1981) and involve challenging the membrane filter with a known quantity (ca. $10^7/cm^2$) of unusually small microorganisms, such as *Brevundimonas diminuta* (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 μm filters without destroying their organized structure.

In some embodiments, the methods disclosed herein comprise sterilizing the formulation (or components thereof) by means of filtration sterilization. In another embodiment the auris-acceptable otic therapeutic agent formulation comprises a particle wherein the particle formulation is suitable for filtration sterilization. In a further embodiment said particle formulation comprises particles of less than 300 nm in size, of less than 200 nm in size, of less than 100 nm in size. In another embodiment the auris-acceptable formulation comprises a particle formulation wherein the sterility of the particle is ensured by sterile filtration of the precursor component solutions. In another embodiment the auris-acceptable formulation comprises a particle formulation wherein the sterility of the particle formulation is ensured by low temperature sterile filtration. In a further embodiment, low temperature sterile filtration is carried out at a temperature between 0 and 30° C., between 0 and 20° C., between 0 and 10° C., between 10 and 30° C., or between 10 and 20° C.

In another embodiment is a process for the preparation of an auris-acceptable particle formulation comprising: filtering the aqueous solution containing the particle formulation at low temperature through a sterilization filter; lyophilizing the sterile solution; and reconstituting the particle formulation with sterile water prior to administration. In some embodiments, a formulation described herein is manufactured as a suspension in a single vial formulation containing the micronized active pharmaceutical ingredient. A single vial formulation is prepared by aseptically mixing a sterile poloxamer solution with sterile micronized active ingredient (e.g., ciprofloxacin) and transferring the formulation to sterile pharmaceutical containers. In some embodiments, a single vial containing a formulation described herein as a suspension is resuspended before dispensing and/or administration.

In specific embodiments, filtration and/or filling procedures are carried out at about 5° C. below the gel temperature (Tgel) of a formulation described herein and with viscosity below a theoretical value of 100 cP to allow for filtration in a reasonable time using a peristaltic pump.

In another embodiment the auris-acceptable otic therapeutic agent formulation comprises a nanoparticle formulation wherein the nanoparticle formulation is suitable for filtration sterilization. In a further embodiment the nanoparticle formulation comprises nanoparticles of less than 300 nm in size, of less than 200 nm in size, or of less than 100 nm in size. In another embodiment the auris-acceptable formulation comprises a microsphere formulation wherein the sterility of the microsphere is ensured by sterile filtration of the precursor organic solution and aqueous solutions. In another embodiment the auris-acceptable formulation comprises a thermoreversible gel formulation wherein the sterility of the gel formulation is ensured by low temperature sterile filtration. In a further embodiment, the low temperature sterile filtration occurs at a temperature between 0 and 30° C., or between 0 and 20° C., or between 0 and 10° C., or between 10 and 30° C., or between 10 and 20° C. In another embodiment is a process for the preparation of an auris-acceptable thermoreversible gel formulation comprising: filtering the aqueous solution containing the thermoreversible gel components at low temperature through a sterilization filter; lyophilizing the sterile solution; and reconstituting the thermoreversible gel formulation with sterile water prior to administration.

In certain embodiments, the active ingredients are dissolved in a suitable vehicle (e.g. a buffer) and sterilized separately (e.g. by heat treatment, filtration, gamma or e-beam radiation). In some instances, the active ingredients are sterilized separately in a dry state. In some instances, the active ingredients are sterilized as a suspension or as a colloidal suspension. The remaining excipients (e.g., fluid gel components present in auris formulations) are sterilized in a separate step by a suitable method (e.g. filtration and/or irradiation of a cooled mixture of excipients); the two solutions that are separately sterilized are then mixed aseptically to provide a final auris formulation. In some instances, the final aseptic mixing is performed just prior to administration of a formulation described herein.

In some instances, conventionally used methods of sterilization (e.g., heat treatment (e.g., in an autoclave), gamma or e-beam irradiation, filtration) lead to irreversible degradation of polymeric components (e.g., thermosetting, gelling or mucoadhesive polymer components) and/or the active agent in the formulation. In some instances, sterilization of an auris formulation by filtration through membranes (e.g., 0.2 μm membranes) is not possible if the formulation comprises thixotropic polymers that gel during the process of filtration.

Accordingly, provided herein are methods for sterilization of auris formulations that prevent degradation of polymeric components (e.g., thermosetting and/or gelling and/or mucoadhesive polymer components) and/or the active agent during the process of sterilization. In some embodiments, degradation of the active agent (e.g., any therapeutic otic agent described herein) is reduced or eliminated through the use of specific pH ranges for buffer components and specific proportions of gelling agents in the formulations. In some embodiments, the choice of an appropriate gelling agent and/or thermosetting polymer allows for sterilization of formulations described herein by filtration. In some embodiments, the use of an appropriate thermosetting polymer and an appropriate copolymer (e.g., a gelling agent) in combination with a specific pH range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the active agent and/or excipients and/or polymeric components during the sterilization step and are rendered substantially free of microbes and/or pyrogens.

Radiation Sterilization

One advantage of radiation sterilization is the ability to sterilize many types of products without heat degradation or other damage. The radiation commonly employed is beta radiation or alternatively, gamma radiation from a $^{60}$Co source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The formulations described herein are also optionally sterilized using beta irradiation. Electron beam (E-beam) irradiation or electron irradiation is a process which involves using electrons, usually of high energy, to treat an object for a variety of purposes. This may take place under elevated temperatures and nitrogen atmosphere. Possible uses for electron irradiation include sterilization. Electron beam processing has the ability to break the chains of DNA in living organisms, such as bacteria, resulting in microbial death and rendering the space they inhabit sterile. E-beam irradiation has been used for the sterilization of medical products and aseptic packaging materials for foods as well as disinfestation, the elimination of live insects from grain, tobacco, and other unprocessed bulk crops. In some embodiments, sterilization with electrons provides quick and reliable sterilization, is compatible with most materials, and does not require any quarantine following the processing. For some materials and products that are sensitive to oxidative effects, radiation tolerance levels for electron beam irradiation may be higher than for gamma exposure. This is due to the higher dose rates and shorter exposure times of e-beam irradiation which have been shown to reduce the degradative effects of oxygen.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the apoptotic agents. The germicidal activity of ethylene oxide, for example, arises from its ability to serve as a reactive alkylating agent. Thus, the sterilization process requires the ethylene oxide vapors to make direct contact with the product to be sterilized.

Microorganisms

Provided herein are auris-acceptable compositions or devices that ameliorate or lessen otic disorders described herein. Further provided herein are methods comprising the administration of said otic compositions. In some embodiments, the compositions or devices are substantially free of microorganisms. Acceptable bioburden or sterility levels are based on applicable standards that define therapeutically acceptable compositions, including but not limited to United States Pharmacopeia Chapters <1111> et seq. For example, acceptable sterility (e.g., bioburden) levels include about 10 colony forming units (cfu) per gram of formulation, about 50 cfu per gram of formulation, about 100 cfu per gram of formulation, about 500 cfu per gram of formulation or about 1000 cfu per gram of formulation. In some embodiments, acceptable bioburden levels or sterility for formulations include less than 10 cfu/mL, less that 50 cfu/mL, less than 500 cfu/mL or less than 1000 cfu/mL microbial agents. In addition, acceptable bioburden levels or sterility include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

Sterility of the auris-acceptable otic therapeutic agent formulation is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, any controlled release formulation described herein has less than about 60 colony forming units (CFU), less than about 50 colony forming units, less than about 40 colony forming units, or less than about 30 colony forming units of microbial agents per gram of formulation. In certain embodiments, the otic formulations described herein are formulated to be isotonic with the endolymph and/or the perilymph.

Endotoxins

Provided herein are otic compositions that ameliorate or lessen otic disorders described herein. Further provided herein are methods comprising the administration of said otic compositions. In some embodiments, the compositions or devices are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins can vary widely, the presence of endotoxins is expressed in "endotoxin units" (EU). One EU is equivalent to 100 picograms of *E. coli* LPS. Humans can develop a response to as little as 5 EU/kg of body weight. The bioburden (e.g., microbial limit) and/or sterility (e.g., absence of microbes) or endotoxin level is expressed in any units as recognized in the art. In certain embodiments, otic compositions described herein contain lower endotoxin levels (e.g. <4 EU/kg of body weight of a subject) when compared to conventionally acceptable endotoxin levels (e.g., 5 EU/kg of body weight of a subject). In some embodiments, the auris-acceptable otic therapeutic agent formulation has less than about 5 EU/kg of body weight of a subject. In other embodiments, the auris-acceptable otic therapeutic agent formulation has less than about 4 EU/kg of body weight of a subject. In additional embodiments, the auris-acceptable otic therapeutic agent formulation has less than about 3 EU/kg of body weight of a subject. In additional embodiments, the auris-acceptable otic therapeutic agent formulation has less than about 2 EU/kg of body weight of a subject.

In some embodiments, the auris-acceptable otic therapeutic agent formulation or device has less than about 5 EU/kg of formulation. In other embodiments, the auris-acceptable otic therapeutic agent formulation has less than about 4 EU/kg of formulation. In additional embodiments, the auris-acceptable otic therapeutic agent formulation has less than about 3 EU/kg of formulation. In some embodiments, the auris-acceptable otic therapeutic agent formulation has less than about 5 EU/kg Product. In other embodiments, the auris-acceptable otic therapeutic agent formulation has less than about 1 EU/kg Product. In additional embodiments, the auris-acceptable otic therapeutic agent formulation has less than about 0.2 EU/kg Product. In some embodiments, the auris-acceptable otic therapeutic agent formulation has less than about 5 EU/g of unit or Product. In other embodiments, the auris-acceptable otic therapeutic agent formulation has less than about 4 EU/g of unit or Product. In additional embodiments, the auris-acceptable otic therapeutic agent formulation has less than about 3 EU/g of unit or Product. In some embodiments, the auris-acceptable otic therapeutic agent formulation has less than about 5 EU/mg of unit or Product. In other embodiments, the auris-acceptable otic therapeutic agent formulation has less than about 4 EU/mg of unit or Product. In additional embodiments, the auris-acceptable otic therapeutic agent formulation has less than about 3 EU/mg of unit or Product. In certain embodiments, otic compositions described herein contain from about 1 to about 5 EU/mL of formulation. In certain embodiments, otic compositions described herein contain from about 2 to about 5 EU/mL of formulation, from about 3 to about 5 EU/mL of formulation, or from about 4 to about 5 EU/mL of formulation.

In certain embodiments, otic compositions or devices described herein contain lower endotoxin levels (e.g. <0.5 EU/mL of formulation) when compared to conventionally acceptable endotoxin levels (e.g., 0.5 EU/mL of formulation). In some embodiments, the auris-acceptable otic therapeutic agent formulation or device has less than about 0.5 EU/mL of formulation. In other embodiments, the auris-acceptable otic therapeutic agent formulation has less than about 0.4 EU/mL of formulation. In additional embodiments, the auris-acceptable otic therapeutic agent formulation has less than about 0.2 EU/mL of formulation.

Pyrogen detection, by way of example only, is performed by several methods. Suitable tests for sterility include tests described in United States Pharmacopoeia (USP) <71> Sterility Tests (23rd edition, 1995). The rabbit pyrogen test and the Limulus amebocyte lysate test are both specified in the United States Pharmacopoeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the Limulus amebocyte lysate test (Taktak et al, J. Pharm. Pharmacol. (1990, 43:578-82). In an additional embodiment, the auris-acceptable otic therapeutic agent formulation is subject to depyrogenation. In a further embodiment, the process for the manufacture of the auris-acceptable otic therapeutic agent formulation comprises testing the formulation for pyrogenicity. In certain embodiments, the formulations described herein are substantially free of pyrogens.

Sterilization of Ciprofloxacin

While pharmaceutical formulations can be sterilized by heat, radiation or filtration, effective sterilization of specific pharmaceutical compositions often presents unique challenge(s). Those challenges sometimes depend on for example, physical and chemical characteristics of the pharmaceutical composition, physical and chemical characteristics of the active agent, physical and chemical characteristics of the carrier materials, physical and chemical characteristics of the auxiliary agents and/or physical and chemical characteristics of the excipients.

For some pharmaceutical compositions comprising particulate active agents, such as micronized active agents, filtration sterilization of the suspension may lead to physical separation of at least a portion of the particulate active agent from the rest of the composition that passes through the sterilization filter. Moreover, the particulate active agent that fails to pass through the sterilization filter may not be sufficiently sterilized.

Radiation or dry heat sterilization of bulk particulate active agent, on the other hand, may require aseptic powder fill or formulation as a part of manufacturing process. For example, while a suspension of micronized ciprofloxacin in an aqueous carrier can be formulated by radiation or dry heat sterilization of bulk ciprofloxacin particles and aseptic compounding of sterilized ciprofloxacin particles and the sterilized aqueous carrier, the process would require customized equipments and/or process design. Alternatively, the micronized ciprofloxacin can be radiation or dry heat sterilized in vials, and subsequently reconstituted with the aqueous carrier (as a diluent component) before administration.

The present disclosure recognizes the technical effect of using a moist heat sterilization process of the ciprofloxacin bulk suspension to manufacture a ready-to-use sterile ciprofloxacin suspension. Moreover, the present disclosure also recognizes the technical effect of particle size and/or particle size distribution of ciprofloxacin suspension on desirable properties such as release characteristics of the drug product. Furthermore, the present disclosure recognizes the technical effect of mixing and/or homogenization during the sterilization process on the particle size and/or particle size distribution of ciprofloxacin in suspension.

Figure 3:
FIG. 3 is a photograph of the aqueous ciprofloxacin suspension in FIG. 2 after cooling down, particularly illustrating the solidification of the suspension.

For example, a reactor with a tri-mixer system is used during heat sterilization of ciprofloxacin suspension to obtain the desired particle size of ciprofloxacin. It is unexpectedly discovered that a 13.4% w/w suspension of ciprofloxacin base (anhydrous) in water, when heated at >121.5° C. for an extended period of time (e.g. 20 minutes), the liquid suspension begins to turn into a solid or semi-solid mass during the cool-down after heat exposure. Eventually, the liquid suspension in some examples solidifies into a dry, hard solid mixture of ciprofloxacin and water, as shown in FIG. 3. This solid mixture cannot be further processed and/or handled, or re-suspended to form the liquid suspension.

Furthermore, the present disclosure recognizes that, if the ciprofloxacin suspension is mixed or homogenized aggressively when it begins to solidify, the suspension can go through the transition and remain a liquid. If the suspension can be maintained as a liquid, a second cycle of heat sterilization at >121.5° C. can be conducted, in which the ciprofloxacin suspension is less likely to solidify during the second cool-down. For example, in a number of large scale manufacturing runs, the mixing tank is opened up during the first cool-down when the suspension started to solidify. As the ciprofloxacin suspension is homogenized or mixed with large Teflon paddles by the operators, it remains a liquid suspension. On a second heat sterilization cycle, the suspension sometimes does not solidify.

Still further, the present disclosure recognizes that that bulk ciprofloxacin free base (anhydrous) can be dry heat sterilized or sterilized by Gamma or E-beam irradiation, and that sterile suspension of ciprofloxacin in water or an aqueous carrier can be prepared by aseptically adding sterilized bulk ciprofloxacin free base (anhydrous) to sterile filtered water or aqueous carrier, followed by extensive mixing. Alternatively, ciprofloxacin free base (hydrate) can be used in the process. While ciprofloxacin free based hydrate is not available under an approved Drug Master File (DMF), it can be produced from either HCl salt or anhydrous free base of ciprofloxacin.

In some embodiments, the method of making sterilized ciprofloxacin compositions disclosed herein includes the steps of: (a) forming an aqueous suspension comprising ciprofloxacin particles; (b) heating the aqueous suspension comprising ciprofloxacin particles at a temperature range of from about 100° C. to about 120° C.; and (c) allowing the aqueous suspension comprising ciprofloxacin particles to cool down.

In some embodiments, the aqueous suspension in step (a) is formed by mixing ciprofloxacin particles with water. In some embodiments, the aqueous suspension in step (a) is formed by homogenizing ciprofloxacin particles in water.

In some embodiments, the aqueous suspension in step (a) is essentially free of organic solvent.

In some embodiments, the ciprofloxacin particles in step (a) are in the form of ciprofloxacin anhydrous particles, ciprofloxacin hydrate particles, or a combination thereof. In some embodiments, the ciprofloxacin particles in step (a) are essentially in the form of ciprofloxacin hydrate particles.

In some embodiments, the ciprofloxacin particles in step (a) are present in the aqueous suspension at a concentration of from about 4 wt % to about 30 wt %. In some embodiments, the ciprofloxacin particles in step (a) are present in the aqueous suspension at a concentration of from about 4 wt % to about 20 wt %. In some embodiments, the ciprofloxacin particles in step (a) are present in the aqueous suspension at a concentration of from about 4 wt % to about 16 wt %.

In some embodiments, the ciprofloxacin particles in step (a) have a D90 of from about 40 μm to about 80 μm. In some embodiments, the ciprofloxacin particles in step (a) have a D90 of from about 45 μm to about 75 μm. In some embodiments, the ciprofloxacin particles in step (a) have a D90 of from about 50 μm to about 70 μm. In some embodiments, the ciprofloxacin particles in step (a) have a D90 of from about 40 μm to about 80 μm.

In some embodiments, the aqueous suspension in step (b) is heated at a temperature of from about 101° C. to about 119° C. In some embodiments, the aqueous suspension in step (b) is heated at a temperature of from about 102° C. to about 118° C. In some embodiments, the aqueous suspension in step (b) is heated at a temperature of from about 103° C. to about 117° C. In some embodiments, the aqueous suspension in step (b) is heated at a temperature of from about 104° C. to about 116° C. In some embodiments, the aqueous suspension in step (b) is heated at a temperature of from about 105° C. to about 115° C.

In some embodiments, the aqueous suspension in step (b) is heated for a period of from about 5 minutes to about 5 hours. In some embodiments, the aqueous suspension in step (b) is heated for a period of from about 10 minutes to about 5 hours. In some embodiments, the aqueous suspension in step (b) is heated for a period of from about 20 minutes to about 5 hours. In some embodiments, the aqueous suspension in step (b) is heated for a period of from about 30 minutes to about 5 hours. In some embodiments, the aqueous suspension in step (b) is heated for a period of from about 40 minutes to about 4 hours. In some embodiments, the aqueous suspension in step (b) is heated for a period of from about 50 minutes to about 3 hours. In some embodiments, the aqueous suspension in step (b) is heated for a period of from about 1 hour to about 2 hours.

In some embodiments, the aqueous suspension in step (b) is heated at a temperature of about 115° C. for a period of about 1 hour. In some embodiments, the aqueous suspension in step (b) is heated at a temperature of about 105° C. for a period of about 2 hour. In some embodiments, the aqueous suspension in step (b) is heated at a temperature of about 110° C. for a period of from about 1 hour to about 2 hours.

In some embodiments, the aqueous suspension in step (b) is heated at a constant temperature within the temperature range. In some embodiments, the aqueous suspension in step (b) is heated at variable temperatures within the temperature range.

In some embodiments, the ciprofloxacin particles in step (b) are homogenized in the aqueous suspension when heated.

In some embodiments, the ciprofloxacin particles in step (c) are essentially in the form of ciprofloxacin hydrate particles.

In some embodiments, the ciprofloxacin particles in step (c) are homogenized in the aqueous suspension during cooling. In some embodiments, the aqueous suspension in step (c) is allowed to cool down to from about 2° C. to about 10° C.

In some embodiments, the ciprofloxacin particles in step (c) have a D90 of from about 5 µm to about 40 µm after cooling down. In some embodiments, the ciprofloxacin particles in step (c) have a D90 of from about 10 µm to about 35 µm after cooling down. In some embodiments, the ciprofloxacin particles in step (c) have a D90 of from about 15 µm to about 25 µm after cooling down.

It is unexpectedly discovered that if a ciprofloxacin suspension is heated sterilized at a temperature too high (e.g. >121.5° C.) or at least initially heated at a temperature too high (e.g. initially heated at 135° C.), the thick suspension becomes thinner. Without wishing to be bound by any particular theory, it is contemplated that ciprofloxacin free base (anhydrous) is converted into ciprofloxacin free base (hydrate) upon mixing with water, and the hydrate form ciprofloxacin free base is reconverted to anhydrous form during the high temperature exposure.

It is also unexpectedly discovered that if the initial ciprofloxacin suspension is heat sterilized at lower sterilization temperatures (e.g. 100° C.-120° C.), the thickness of the suspension does not change as much as when the suspension is heated at the higher temperature. In some embodiments, the suspension remains thick. Furthermore, the suspension heated at the lower temperature does not solidify during cool-down as the suspension heated at the higher temperature. Without wishing to be bound by any particular theory, it is contemplated that that ciprofloxacin free base (anhydrous) is converted into ciprofloxacin free base (hydrate) upon mixing with water, and the hydrate form ciprofloxacin free base remains in hydrate form during the lower temperature exposure (e.g. 100° C.-120° C.).

Furthermore, ciprofloxacin solubility significantly increases between room temperature to the higher sterilization temperature (e.g. 121° C. and above). For example, it is measured to increase from 30-60 µg/mL to 10-15 mg/mL. Without wishing to be bound by any particular theory, it is contemplated that the solubility increase can contribute to the solidification of ciprofloxacin suspension when heated at higher temperatures (e.g. 121° C. and above). For example, at higher temperature, more ciprofloxacin dissolves into the water and then when cooled back down, the ciprofloxacin precipitates/crystallizes back out of solution. It can grow onto existing crystals and lead to long needles of solid ciprofloxacin, making the solidifying mass difficult to break down. The present disclosure recognizes the technical effects of solubility change and crystallization process on heat sterilization of ciprofloxacin suspensions.

Otic Ciprofloxacin Formulations
Certain Definitions

The term "auris-acceptable" with respect to a formulation, composition or ingredient, as used herein, includes having no persistent detrimental effect on the auris structure of the subject being treated. By "auris-pharmaceutically acceptable," as used herein, refers to a material, such as a carrier or diluent, which does not abrogate the biological activity or properties of the compound in reference to the auris structure, and is relatively or is reduced in toxicity to the auris structure, i.e., the material is administered to an individual without causing undesirable biological effects or interacting in a deleterious manner with any of the components of the composition in which it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

"Auris interna" refers to the inner ear, including the cochlea and the vestibular labyrinth, and the round window that connects the cochlea with the middle ear.

"Auris media" refers to the middle ear, including the tympanic cavity, auditory ossicles and oval window, which connects the middle ear with the inner ear.

"Balance disorder" refers to a disorder, illness, or condition which causes a subject to feel unsteady, or to have a sensation of movement. Included in this definition are dizziness, vertigo, disequilibrium, and pre-syncope. Diseases which are classified as balance disorders include, but are not limited to, Ramsay Hunt's Syndrome, Meniere's Disease, mal de debarquement, benign paroxysmal positional vertigo, and labyrinthitis.

"Blood plasma concentration" refers to the concentration of compounds provided herein in the plasma component of blood of a subject.

"Carrier materials" are excipients that are compatible with moist-heat, the auris structure target site and the release profile properties of the auris-acceptable pharmaceutical formulations. Such carrier materials include, e.g., binders, suspending agents, disintegration agents, filling agents, surfactants, solubilizers, stabilizers, lubricants, wetting agents, diluents, and the like. "Auris-pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

The term "diluent" refers to chemical compounds that are used to dilute the antimicrobial agent prior to delivery and which are compatible with the auris structure target site.

"Dispersing agents," and/or "viscosity modulating agents" are materials that control the diffusion and homogeneity of the antimicrobial agent through liquid media. Examples of diffusion facilitators/dispersing agents include but are not limited to hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers; and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also be used as dispersing agents. Dispersing agents useful in liposomal dispersions and self-emulsifying dispersions of the antimicrobial agents disclosed herein are dimyristoyl phosphatidyl choline, natural phosphatidyl choline from eggs, natural phosphatidyl glycerol from eggs, cholesterol and isopropyl myristate.

"Drug absorption" or "absorption" refers to the process of movement of the ciprofloxacin from the localized site of administration into the ear. The terms "co-administration" or the like, as used herein, are meant to encompass administration of the ciprofloxacin to a single patient, and are intended to include treatment regimens in which the ciprofloxacin are administered by the same or different route of administration or at the same or different time.

The terms "effective amount" or "therapeutically effective amount," as used herein, refer to a sufficient amount of the ciprofloxacin being administered that would be expected to relieve to some extent one or more of the symptoms of the disease or condition being treated. For example, the result of administration of ciprofloxacin disclosed herein is reduction and/or alleviation of the signs, symptoms, or causes of tinnitus or balance disorders. For example, an "effective amount" for therapeutic uses is the amount of ciprofloxacin, including a formulation as disclosed herein required to provide a decrease or amelioration in disease symptoms without undue adverse side effects. The term "therapeutically effective amount" includes, for example, a prophylactically effective amount. An "effective amount" of ciprofloxacin disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate release dosing format based upon pharmacokinetic and pharmacodynamic considerations.

The terms "enhance" or "enhancing" refers to an increase or prolongation of either the potency or duration of a desired effect of ciprofloxacin, or a diminution of any adverse symptomatology that is consequent upon the administration of the therapeutic agent. Thus, in regard to enhancing the effect of ciprofloxacin disclosed herein, the term "enhancing" refers to the ability to increase or prolong, either in potency or duration, the effect of other therapeutic agents that are used in combination with ciprofloxacin disclosed herein. An "enhancing-effective amount," as used herein, refers to an amount of ciprofloxacin or other therapeutic agent which is adequate to enhance the effect of another therapeutic agent or ciprofloxacin of the target auris structure in a desired system. When used in a patient, amounts effective for this use will depend on the severity and course of the disease, disorder or condition, previous therapy, the patient's health status and response to the drugs, and the judgment of the treating physician.

"Pharmacodynamics" refers to the factors which determine the biologic response observed relative to the concentration of drug at the desired site within the auris media and/or auris interna.

"Pharmacokinetics" refers to the factors which determine the attainment and maintenance of the appropriate concentration of drug at the desired site within the auris media and/or auris interna.

The term "otic intervention" means an external insult or trauma to one or more auris structures and includes implants, otic surgery, injections, cannulations, or the like. Implants include auris-interna or auris-media medical devices, examples of which include cochlear implants, hearing sparing devices, hearing-improvement devices, tympanostomy tubes, short electrodes, micro-prostheses or piston-like prostheses; needles; stem cell transplants; drug delivery devices; any cell-based therapeutic; or the like. Otic surgery includes middle ear surgery, inner ear surgery, tympanostomy, cochleostomy, labyrinthotomy, mastoidectomy, stapedectomy, stapedotomy, endolymphatic sacculotomy or the like. Injections include intratympanic injections, intracochlear injections, injections across the round window membrane or the like. Cannulations include intratympanic, intracochlear, endolymphatic, perilymphatic or vestibular cannulations or the like.

In prophylactic applications, compositions comprising ciprofloxacin described herein are administered to a patient susceptible to or otherwise at risk of a particular disease, disorder or condition. For example, such conditions include and are not limited to otitis externa, otitis media, Ramsay Hunt syndrome, otosyphilis, AIED, Meniere's disease, and vestibular neuronitis. Such an amount is defined to be a "prophylactically effective amount or dose." In this use, the precise amounts also depend on the patient's state of health, weight, and the like.

The term "essentially free of organic solvent" means less than 5% by weight of the active agent are degradation products of the active agent. In further embodiments, the term means less than 3% by weight of the active agent are degradation products of the active agent. In yet further embodiments, the term means less than 2% by weight of the active agent are degradation products of the active agent. In further embodiments, the term means less than 1% by weight of the active agent are degradation products of the active agent.

As used herein "essentially in the form of micronized powder" includes, by way of example only, greater than 70% by weight of the active agent is in the form of micronized particles of the active agent. In further embodiments, the term means greater than 80% by weight of the active agent is in the form of micronized particles of the active agent. In yet further embodiments, the term means greater than 90% by weight of the active agent is in the form of micronized particles of the active agent.

"Ready-to-use" refers to pharmaceutical compositions or medical products that can be used without the needs of further changing, modifying, or optimizing the composition or the product prior to administration, for example through dilution, reconstitution, further sterilization, etc.

"Stabilizers" refers to compounds such as any antioxidation agents, buffers, acids, preservatives and the like that are compatible with the environment of the middle or inner ear. Stabilizers include but are not limited to agents that will do any of (1) improve the compatibility of excipients with a container, or a delivery system, including a syringe or a glass bottle, (2) improve the stability of a component of the composition, or (3) improve formulation stability.

As used herein, the term "subject" is used to mean an animal, preferably a mammal, including a human or non-human. The terms patient and subject may be used interchangeably.

The terms "treat," "treating" or "treatment," as used herein, include alleviating, abating or ameliorating a disease or condition, for example tinnitus, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features, and advantages of the methods and compositions described herein will become apparent from the following detailed description. It should be understood, however, that the detailed description and the specific examples, while indicating specific embodiments, are given by way of illustration only.

Method of Formulation

In some embodiments, the methods of making sterilized ciprofloxacin compositions further include the step of: (d) combining the cooled aqueous suspension comprising ciprofloxacin particles with a sterilized aqueous solution comprising a thermoreversible polymer to form an otic formulation.

In some embodiments, the thermoreversible polymer is a polyoxyethylene-polyoxypropylene triblock copolymer. In some embodiments, the thermoreversible polymer is poloxamer 407.

In some embodiments, the aqueous solution further comprises a buffer agent. In some embodiments, the buffer agent is tromethamine.

In some embodiments, the aqueous solution further comprises a pH adjusting agent in an amount to adjust the pH of the aqueous solution to from about 7.0 to about 8.0. In some embodiments, the pH adjusting agent is hydrochloric acid.

In some embodiments, the aqueous solution further comprises an osmolarity modifier. In some embodiments, the osmolarity modifier is sodium chloride.

In some embodiments, the aqueous solution is sterilized through filtration sterilization, heat sterilization, or radiation sterilization. In some embodiments, the aqueous solution is sterilized through filtration sterilization. In some embodiments, the aqueous solution is sterilized by passing through a cold sterilization filter.

In some embodiments, the aqueous solution is allowed to cool down to from about 2° C. to about 10° C.

In some embodiments, the aqueous suspension and the aqueous solution are combined under aseptic condition.

In some embodiments, the otic formulation comprises from about 5 wt % to about 7 wt % of ciprofloxacin. In some embodiments, the otic formulation comprises from about 5.5 wt % to about 6.5 wt % of ciprofloxacin.

In some embodiments, the otic formulation comprises from about 14 wt % to about 19 wt % of the thermoreversible polymer. In some embodiments, the otic formulation comprises from about 15 wt % to about 17 wt % of the thermoreversible polymer. In some embodiments, the otic formulation comprises from about 15.5 wt % to about 16.5 wt % of the thermoreversible polymer.

In some embodiments, the otic formulation has a pH of from about 7.0 to about 8.0.

In some embodiments, the otic formulation has an osmolarity of from about 270 mOsm/L to about 320 mOsm/L.

In some embodiments, the otic formulation has less than about 50 colony forming units (cfu) of microbiological agents per gram of formulation.

In some embodiments, the otic formulation has less than about 5 endotoxin units (EU) per kg of body weight of a subject.

In some embodiments, the otic formulation has a gelation temperature between about 19° C. to about 42° C.

Otic Gel Formulations

Gels have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophilic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

In one embodiment the enhanced viscosity auris-acceptable formulation described herein is not a liquid at room temperature. In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. In one embodiment, administration of any formulation described herein at about body temperature reduces or inhibits vertigo associated with intratympanic administration of otic formulations. Included within the definition of body temperature is the body temperature of a healthy individual, or an unhealthy individual, including an individual with a fever (up to ~42° C.). In some embodiments, the pharmaceutical compositions or devices described herein are liquids at about room temperature and are administered at or about room temperature, reducing or ameliorating side effects such as, for example, vertigo.

Polymers composed of polyoxypropylene and polyoxyethylene form thermoreversible gels when incorporated into aqueous solutions. These polymers have the ability to change from the liquid state to the gel state at temperatures close to body temperature, therefore allowing useful formulations that are applied to the targeted auris structure(s). The liquid state-to-gel state phase transition is dependent on the polymer concentration and the ingredients in the solution.

Poloxamer 407 is a thermoreversible polymer composed of polyoxyethylene-polyoxypropylene copolymers. Other polyoxyethylene-polyoxypropylene copolymers (i.e. poloxamers) include 188 (F-68 grade), 237 (F-87 grade), 338 (F-108 grade). Aqueous solutions of poloxamers are stable in the presence of acids, alkalis, and metal ions. Poloxamer 407 is a commercially available and can be further purified by suitable methods that will enhance gelation properties of the polymer. It contains approximately 70% ethylene oxide, which accounts for its hydrophilicity. It is one of the series of poloxamer ABA block copolymers, whose members share the chemical formula shown below.

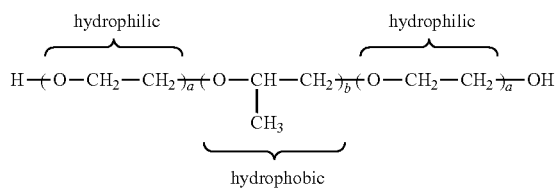

Some aqueous poloxamer solutions (e.g. poloxamer 407) transform from low viscosity solutions to solid gels on heating to body temperature (e.g. after administration into the ear). Furthermore, poloxamer 407 has good solubilizing capacity, low toxicity and is, therefore, considered a good medium for drug delivery systems.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PGLA copolymer of 50:50 poly (DL-lactide-co-glycolide) and is 10% w/w of PEG and has a molecular weight of about 6000.

ReGel® is a trade name of MacroMed Incorporated for a class of low molecular weight, biodegradable block copolymers having reverse thermal gelation properties as described in U.S. Pat. Nos. 6,004,573, 6,117,949, 6,201,072, and 6,287,588. It also includes biodegradable polymeric drug carriers disclosed in pending U.S. patent application Ser. Nos. 09/906,041, 09/559,799 and 10/919,603. The biodegradable drug carrier comprises ABA-type or BAB-type triblock copolymers or mixtures thereof, wherein the A-blocks are relatively hydrophobic and comprise biodegradable polyesters or poly(orthoester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 Daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly(orthoester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof and having an average molecular weight of between about 600 and 3000 Daltons. The hydrophilic B-block segment is preferably polyethylene glycol (PEG) having an average molecular weight of between about 500 and 2200 Daltons.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermoreversible gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermoreversible gel polymer.

In one embodiment are auris-acceptable pharmaceutical gel formulations which do not require the use of an added viscosity enhancing agent. Such gel formulations incorporate at least one pharmaceutically acceptable buffer. In one aspect is a gel formulation comprising ciprofloxacin and a pharmaceutically acceptable buffer. In another embodiment, the pharmaceutically acceptable excipient or carrier is a gelling agent.

Also described herein are controlled release formulations or devices comprising ciprofloxacin and a viscosity enhancing agent. Suitable viscosity-enhancing agents include by way of example only, gelling agents and suspending agents. In one embodiment, the enhanced viscosity formulation does not include a buffer. In other embodiments, the enhanced viscosity formulation includes a pharmaceutically acceptable buffer. Sodium chloride or other tonicity agents are optionally used to adjust tonicity, if necessary.

By way of example only, the auris-acceptable viscosity agents include hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted auris structure include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly (methoxyethoxyethyl methacrylate), hydroxypropyl cellulose, hydroxypropylmethylcellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with ciprofloxacin disclosed herein acts as a controlled release formulation, restricting the diffusion of ciprofloxacin from the formulation. Moreover, the combination of carboxymethylated chitosan and alginate is optionally used to assist in increasing the permeability of ciprofloxacin into the ear.

In some embodiments is an enhanced viscosity formulation, comprising from about 0.1 mM and about 100 mM of ciprofloxacin, a pharmaceutically acceptable viscosity agent, and water for injection, the concentration of the viscosity agent in the water being sufficient to provide an enhanced viscosity formulation with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of ciprofloxacin. In highly concentrated samples, the biocompatible enhanced viscosity formulation comprises at least about 25%, at least about 35%, at least about 45%, at least about 55%, at least about 65%, at least about 75%, at least about 85%, at least about 90% or at least about 95% or more by weight of ciprofloxacin.

In some embodiments, the viscosity of the gel formulations presented herein is measured by any means described. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

In one embodiment, the pharmaceutically acceptable enhanced viscosity auris-acceptable formulation comprises ciprofloxacin and at least one gelling agent. Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel formulations presented herein.

In some embodiments, the otic therapeutic agents disclosed herein are dispensed as an auris-acceptable paint. As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent which may be lost and correspondingly increases the amount delivered to the subject. By way of non-limiting example, paints include collodions (e.g. Flexible Collodion, USP), and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers. For additional disclosures regarding paints, see *Remington: The Science and Practice of Pharmacy* which is hereby incorporated with respect to this subject matter. The paints contemplated for use herein, are flexible such that they do not interfere with the propagation of pressure waves through the ear. Further, the paints may be applied as a liquid (i.e. solution, suspension, or emulsion), a semisolid (i.e. a gel, foam, paste, or jelly) or an aerosol.

In some embodiments, the otic therapeutic agents disclosed herein are dispensed as a controlled-release foam. Examples of suitable foamable carriers for use in the compositions disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic side-chains, cellulose and derivatives thereof, agar and derivatives thereof, such as agar stabilized with polyacrylamide, polyethylene oxides, glycol methacrylates, gelatin, gums such as xanthum, guar, karaya, gellan, arabic, tragacanth and locust bean gum, or combinations thereof. Also suitable are the salts of the aforementioned carriers, for example, sodium alginate. The formulation optionally further comprises a foaming agent, which promotes the formation of the foam, including a surfactant or external propellant. Examples of suitable foaming agents include cetrimide, lecithin, soaps, silicones and the like. Commercially available surfactants such as Tween® are also suitable.

Other useful gel formulations are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the ciprofloxacin formulations described herein. In some embodiments, auris-acceptable gels include, but are not limited to, alginate hydrogels SAF®-Gel (ConvaTec, Princeton, N.J.), Duoderm® Hydroactive Gel (ConvaTec), Nu-gel® (Johnson & Johnson Medical, Arlington, Tex.); Carrasyn®(V) Acemannan Hydrogel (Carrington Laboratories, Inc., Irving, Tex.); glycerin gels Elta® Hydrogel (Swiss-American Products, Inc., Dallas, Tex.) and K-Y® Sterile (Johnson & Johnson). In further embodiments, biodegradable biocompatible gels also represent compounds present in auris-acceptable formulations disclosed and described herein.

In some embodiments, the amount of thermoreversible polymer in any formulation described herein is about 10%, about 15%, about 20%, about 25%, about 30%, about 35% or about 40% of the total weight of the formulation. In some embodiments, the amount of thermoreversible polymer in any formulation described herein is about 10%, about 11%, about 12%, about 13%, about 14%, about 15%, about 16%, about 17%, about 18%, about 19%, about 20%, about 21%, about 22%, about 23%, about 24% or about 25% of the total weight of the formulation. In some embodiments, the amount of thermoreversible polymer (e.g., poloxamer 407) in any formulation described herein is about 7.5% of the total weight of the formulation. In some embodiments, the amount of thermoreversible polymer (e.g., poloxamer 407) in any formulation described herein is about 10% of the total weight of the formulation. In some embodiments, the amount of thermoreversible polymer (e.g., poloxamer 407) in any formulation described herein is about 11% of the total weight of the formulation. In some embodiments, the amount of thermoreversible polymer (e.g., poloxamer 407) in any formulation described herein is about 12% of the total weight of the formulation. In some embodiments, the amount of thermoreversible polymer (e.g., poloxamer 407) in any formulation described herein is about 13% of the total weight of the formulation. In some embodiments, the amount of thermoreversible polymer (e.g., poloxamer 407) in any formulation described herein is about 14% of the total weight of the formulation. In some embodiments, the amount of thermoreversible polymer (e.g., poloxamer 407) in any formulation described herein is about 15% of the total weight of the formulation. In some embodiments, the amount of thermoreversible polymer (e.g., poloxamer 407) in any formulation described herein is about 16% of the total weight of the formulation. In some embodiments, the amount of thermoreversible polymer (e.g., poloxamer 407) in any formulation described herein is about 17% of the total weight of the formulation. In some embodiments, the amount of thermoreversible polymer (e.g., poloxamer 407) in any formulation described herein is about 18% of the total weight of the formulation. In some embodiments, the amount of thermoreversible polymer (e.g., poloxamer 407) in any formulation described herein is about 19% of the total weight of the formulation. In some embodiments, the amount of thermoreversible polymer (e.g., poloxamer 407) in any formulation described herein is about 20% of the total weight of the formulation. In some embodiments, the amount of thermoreversible polymer (e.g., poloxamer 407) in any formulation described herein is about 21% of the total weight of the formulation. In some embodiments, the amount of thermoreversible polymer (e.g., poloxamer 407) in any formulation described herein is about 23% of the total weight of the formulation. In some embodiments, the amount of thermoreversible polymer (e.g., poloxamer 407) in any formulation described herein is about 25% of the total weight of the formulation. In some embodiments, the amount of thickening agent (e.g., a gelling agent) in any formulation described herein is about 1%, about 5%, about 10%, or about 15% of the total weight of the formulation. In some embodiments, the amount of thickening agent (e.g., a gelling agent) in any formulation described herein is about 0.5%, about 1%, about 1.5%, about 2%, about 2.5%, about 3%, about 3.5%, about 4%, about 4.5%, or about 5% of the total weight of the formulation.

In some formulations developed for administration to a mammal, and for compositions formulated for human administration, the auris-acceptable gel comprises substantially all of the weight of the composition. In other embodiments, the auris-acceptable gel comprises as much as about 98% or about 99% of the composition by weight. This is desirous when a substantially non-fluid, or substantially viscous formulation is needed. In a further embodiment, when slightly less viscous, or slightly more fluid auris-acceptable pharmaceutical gel formulations are desired, the biocompatible gel portion of the formulation comprises at least about 50% by weight, at least about 60% by weight, at least about 70% by weight, or even at least about 80% or 90% by weight of the compound. All intermediate integers within these ranges are contemplated to fall within the scope of this disclosure, and in some alternative embodiments, even more fluid (and consequently less viscous) auris-acceptable gel compositions are formulated, such as for example, those in which the gel or matrix component of the mixture comprises not more than about 50% by weight, not more than about 40% by weight, not more than about 30% by weight, or even those than comprise not more than about 15% or about 20% by weight of the composition.

Concentration of Ciprofloxacin

In some embodiments, the compositions described herein have a concentration of active pharmaceutical ingredient between about 0.01% to about 90%, between about 0.01% to about 50%, between about 0.1% to about 70%, between about 0.1% to about 50%, between about 0.1% to about 40%, between about 0.1% to about 30%, between about 0.1% to about 20%, between about 0.1% to about 10%, or between about 0.1% to about 5%, of the active ingredient, or pharmaceutically acceptable prodrug or salt thereof, by weight of the composition. In some embodiments, the compositions described herein have a concentration of active pharmaceutical agent, or pharmaceutically acceptable prodrug or salt thereof, between about 1% to about 50%, between about 5% to about 50%, between about 10% to about 40%, or between about 10% to about 30%, of the active ingredient, or pharmaceutically acceptable prodrug or salt thereof, by weight of the composition. In some embodiments, formulations described herein comprise about 70% by weight of ciprofloxacin, or pharmaceutically acceptable prodrug or salt thereof, by weight of the formulation. In some embodiments, formulations described herein comprise about 60% by weight of ciprofloxacin, or pharmaceutically acceptable prodrug or salt thereof, by weight of the formulation. In some embodiments, formulations described herein comprise about 50% by weight of ciprofloxacin, or pharmaceutically acceptable prodrug or salt thereof, by weight of the formulation. In some embodiments, formulations described herein comprise about 40% by weight of ciprofloxacin, or pharmaceutically acceptable prodrug or salt thereof, by weight of the formulation. In some embodiments, formulations described herein comprise about 30% by weight, or pharmaceutically acceptable prodrug or salt thereof, of ciprofloxacin by weight of the formulation. In some embodiments, formulations described herein comprise about 20% by weight of ciprofloxacin, or pharmaceutically acceptable prodrug or salt thereof, by weight of the formulation. In some embodiments, formulations described herein comprise about 15% by weight of ciprofloxacin, or pharmaceutically acceptable prodrug or salt thereof, by weight of the formulation. In some embodiments, formulations described herein comprise about 10% by weight of ciprofloxacin by weight of the formulation. In some embodiments, formulations described herein comprise about 5% by weight ciprofloxacin, or pharmaceutically acceptable prodrug or salt thereof, by weight of the formulation. In some embodiments, formulations described herein comprise about 2.5% by weight of ciprofloxacin, or pharmaceutically acceptable prodrug or salt thereof, by weight of the formulation. In some embodiments, formulations described herein comprise about 1% by weight of ciprofloxacin, or pharmaceutically acceptable prodrug or salt thereof, by weight of the formulation. In some embodiments, formulations described herein comprise about 0.5% by weight of ciprofloxacin, or pharmaceutically acceptable prodrug or salt thereof, by weight of the formulation. In some embodiments, formulations described herein comprise about 0.1% by weight of ciprofloxacin, or pharmaceutically acceptable prodrug or salt thereof, by weight of the formulation. In some embodiments, formulations described herein comprise about 0.01% by weight of ciprofloxacin, or pharmaceutically acceptable prodrug or salt thereof, by weight of the formulation. In some embodiments, the formulations described herein have a concentration of active pharmaceutical ingredient, or pharmaceutically acceptable prodrug or salt thereof, between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the ciprofloxacin, or pharmaceutically acceptable prodrug or salt thereof, by volume of the formulation.

Osmolarity

In some embodiments, an otic composition or device disclosed herein is formulated to provide an ionic balance that is compatible with inner ear fluids (e.g., endolymph and/or perilymph).

In certain instances, the ionic composition of the endolymph and perilymph regulate the electrochemical impulses of hair cells and thus hearing. In certain instances, changes in the conduction of electrochemical impulses along otic hair cells results in hearing loss. In certain instances, changes in the ionic balance of the endolymph or perilymph results in complete hearing loss. In certain instances, changes in the ionic balance of the endolymph or perilymph results in partial hearing loss. In certain instances, changes in the ionic balance of the endolymph or perilymph results in permanent hearing loss. In certain instances, changes in the ionic balance of the endolymph or perilymph results in temporary hearing loss.

In some embodiments, a composition or device disclosed herein is formulated in order to not disrupt the ionic balance of the endolymph. In some embodiments, a composition or device disclosed herein has an ionic balance that is the same as or substantially the same as the endolymph. In some embodiments, a composition or device disclosed herein does not does not disrupt the ionic balance of the endolymph so as to result in partial or complete hearing loss. In some embodiments, a composition or device disclosed herein does not does not disrupt the ionic balance of the endolymph so as to result in temporary or permanent hearing loss.

In some embodiments, a composition or device disclosed herein does not substantially disrupt the ionic balance of the perilymph. In some embodiments, a composition or device disclosed herein has an ionic balance that is the same as or substantially the same as the perilymph. In some embodiments, a composition or device disclosed herein does not result in partial or complete hearing loss as the composition or device does not disrupt the ionic balance of the perilymph. In some embodiments, a composition or device disclosed herein does not result in temporary or permanent hearing loss as the composition or device does not disrupt the ionic balance of the perilymph.

As used herein, "practical osmolarity/osmolarity" or "deliverable osmolarity/osmolarity" means the osmolarity/osmolarity of a composition or device as determined by measuring the osmolarity/osmolarity of the active agent and all excipients except the gelling and/or the thickening agent (e.g., polyoxyethylene-polyoxypropylene copolymers, carboxymethylcellulose or the like). The practical osmolarity of a composition or device disclosed herein is measured by a suitable method, e.g., a freezing point depression method as described in Viegas et. al., *Int. J. Pharm.*, 1998, 160, 157-162. In some instances, the practical osmolarity of a composition or device disclosed herein is measured by vapor pressure osmometry (e.g., vapor pressure depression method) that allows for determination of the osmolarity of a composition or device at higher temperatures. In some instances, vapor pressure depression method allows for determination of the osmolarity of a composition or device comprising a gelling agent (e.g., a thermoreversible polymer) at a higher temperature wherein the gelling agent is in the form of a gel.

In some embodiments, the osmolarity at a target site of action is about the same as the delivered osmolarity (i.e., osmolarity of materials that cross or penetrate to the target site) of a composition or device described herein. In some embodiments, a composition or device described herein has a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The practical osmolality of an otic composition or device disclosed herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a composition or device described herein has a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

The main cation present in the endolymph is potassium. In addition the endolymph has a high concentration of positively charged amino acids. The main cation present in the perilymph is sodium. In certain instances, the ionic composition of the endolymph and perilymph regulate the electrochemical impulses of hair cells. In certain instances, any change in the ionic balance of the endolymph or perilymph results in a loss of hearing due to changes in the conduction of electrochemical impulses along otic hair cells. In some embodiments, a composition disclosed herein does not disrupt the ionic balance of the perilymph. In some embodiments, a composition disclosed herein has an ionic balance that is the same as or substantially the same as the perilymph. In some embodiments, a composition disclosed herein does not disrupt the ionic balance of the endolymph. In some embodiments, a composition disclosed herein has an ionic balance that is the same as or substantially the same as the endolymph. In some embodiments, an otic formulation described herein is formulated to provide an ionic balance that is compatible with inner ear fluids (e.g., endolymph and/or perilymph).

In some embodiments, the deliverable osmolarity of any formulation described herein is designed to be isotonic with the targeted otic structure (e.g., endolymph, perilymph or the like). In specific embodiments, auris compositions described herein are formulated to provide a delivered perilymph-suitable osmolarity at the target site of action of about 250 to about 320 mOsm/L; and preferably about 270 to about 320 mOsm/L. In specific embodiments, auris compositions described herein are formulated to provide a delivered perilymph-suitable osmolarity at the target site of action of about 250 to about 320 mOsm/kg $H_2O$; or an osmolality of about 270 to about 320 mOsm/kg $H_2O$. In specific embodiments, the deliverable osmolarity/osmolarity of the formulations (i.e., the osmolarity/osmolarity of the formulation in the absence of gelling or thickening agents (e.g., thermoreversible gel polymers) is adjusted, for example, by the use of appropriate salt concentrations (e.g., concentration of potassium or sodium salts) or the use of tonicity agents which renders the formulations endolymph-compatible and/or perilymph-compatible (i.e. isotonic with the endolymph and/or perilymph) upon delivery at the target site. The osmolarity of a formulation comprising a thermoreversible gel polymer is an unreliable measure due to the association of varying amounts of water with the monomeric units of the polymer. The practical osmolarity of a formulation (i.e., osmolarity in the absence of a gelling or thickening agent (e.g. a thermoreversible gel polymer) is a reliable measure and is measured by any suitable method (e.g., freezing point depression method, vapor depression method). In some instances, the formulations described herein provide a deliverable osmolarity (e.g., at a target site (e.g., perilymph) that causes minimal disturbance to the environment of the ear and causes minimum discomfort (e.g., vertigo and/or nausea) to a mammal upon administration.

In some embodiments, any formulation described herein is isotonic with the perilymph and/or endolymph. Isotonic formulations are provided by the addition of a tonicity agent. Suitable tonicity agents include, but are not limited to any pharmaceutically acceptable sugar, salt or any combinations or mixtures thereof, such as, but not limited to dextrose, glycerin, mannitol, sorbitol, sodium chloride, and other electrolytes. In some embodiments, tonicity agents are nonototoxic.

Useful auris compositions include one or more salts in an amount required to bring osmolarity of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

pH

The endolymph and the perilymph have a pH that is close to the physiological pH of blood. The endolymph has a pH range of about 7.2-7.9; the perilymph has a pH range of about 7.2-7.4. The in situ pH of the proximal endolymph is about 7.4 while the pH of distal endolymph is about 7.9.

In other embodiments, useful auris-acceptable ciprofloxacin formulations also include one or more pH adjusting agents or buffering agents to provide an endolymph or perilymph suitable pH. Suitable pH adjusting agents or buffers include, but are not limited to acetate, bicarbonate, ammonium chloride, citrate, phosphate, pharmaceutically acceptable salts thereof and combinations or mixtures thereof. Such pH adjusting agents and buffers are included in an amount required to maintain pH of the composition between a pH of about 5 and about 9, in one embodiment a pH between about 6.5 to about 7.5, and in yet another embodiment at a pH of about 6.5, 6.6, 6.7, 6.8, 6.9, 7.0, 7.1, 7.2, 7.3, 7.4, 7.5. In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the auris media or auris interna's natural buffering system, or does not interfere with the natural pH of the endolymph or perilymph. In some embodiments, from about 10 μM to about 200 mM concentration of a buffer is present in the gel formulation. In certain embodiments, from about a 5 mM to about a 200 mM concentration of a buffer is present. In certain embodiments, from about a 20 mM to about a 100 mM concentration of a buffer is present. In one embodiment is a buffer such as acetate or citrate at slightly acidic pH. In one embodiment the buffer is a sodium acetate buffer having a pH of about 4.5 to about 6.5. In one embodiment the buffer is a sodium citrate buffer having a pH of about 5.0 to about 8.0, or about 5.5 to about 7.0.

In an alternative embodiment, the buffer used is tris (hydroxymethyl)aminomethane, bicarbonate, carbonate or phosphate at slightly basic pH. In one embodiment, the buffer is a sodium bicarbonate buffer having a pH of about 6.5 to about 8.5, or about 7.0 to about 8.0. In another embodiment the buffer is a sodium phosphate dibasic buffer having a pH of about 6.0 to about 9.0.

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the body's natural buffering system.

In one embodiment, diluents are also used to stabilize compounds because they can provide a more stable environment. Salts dissolved in buffered solutions (which also can provide pH control or maintenance) are utilized as diluents in the art, including, but not limited to a phosphate buffered saline solution.

In some embodiments, any gel formulation described herein has a pH that allows for sterilization (e.g., by filtration or aseptic mixing or heat treatment and/or autoclaving (e.g., terminal sterilization) of a gel formulation without degradation of the ciprofloxacin or the polymers comprising the gel. In order to reduce hydrolysis and/or degradation of the otic agent and/or the gel polymer during sterilization, the buffer pH is designed to maintain pH of the formulation in the 7-8 range during the process of sterilization (e.g., high temperature autoclaving).

In specific embodiments, any gel formulation described herein has a pH that allows for terminal sterilization (e.g., by heat treatment and/or autoclaving) of a gel formulation without degradation of the ciprofloxacin or the polymers comprising the gel. For example, in order to reduce hydrolysis and/or degradation of the otic agent and/or the gel polymer during autoclaving, the buffer pH is designed to maintain pH of the formulation in the 7-8 range at elevated temperatures. Any appropriate buffer is used depending on the otic agent used in the formulation. In some instances, since $pK_a$ of TRIS decreases as temperature increases at approximately −0.03/° C. and $pK_a$ of PBS increases as temperature increases at approximately 0.003/° C., autoclaving at 250° F. (121° C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. Degradation of an otic agent is reduced by the use of an appropriate combination of a buffer and polymeric additives (e.g. CMC) as described herein.

In some embodiments, a formulation pH of between about 5.0 and about 9.0, between about 5.5 and about 8.5, between about 6.0 and about 7.6, between about 7 and about 7.8, between about 7.0 and about 7.6, between about 7.2 and 7.6, or between about 7.2 and about 7.4 is suitable for sterilization (e.g., by filtration or aseptic mixing or heat treatment and/or autoclaving (e.g., terminal sterilization)) of auris formulations described herein. In specific embodiments a formulation pH of about 6.0, about 6.5, about 7.0, about 7.1, about 7.2, about 7.3, about 7.4, about 7.5, or about 7.6 is suitable for sterilization (e.g., by filtration or aseptic mixing or heat treatment and/or autoclaving (e.g., terminal sterilization)) of any composition described herein. In some embodiments, the pharmaceutical formulations described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to pH over a period of at least about 1 week. Also described herein are formulations that are stable with respect to pH over a period of at least about 1 month.

Particle Size

Size reduction is used to increase surface area and/or modulate formulation dissolution properties. It is also used to maintain a consistent average particle size distribution (PSD) (e.g., micrometer-sized particles, nanometer-sized particles or the like) for any formulation described herein. In some embodiments, any formulation described herein comprises multiparticulates, i.e., a plurality of particle sizes (e.g., micronized particles, nano-sized particles, non-sized particles, colloidal particles); i.e., the formulation is a multiparticulate formulation. In some embodiments, any formulation described herein comprises one or more multiparticulate (e.g., micronized) therapeutic agents. Micronization is a process of reducing the average diameter of particles of a solid material. Micronized particles are from about micrometer-sized in diameter to about nanometer-sized in diameter. In some embodiments, the average diameter of particles in a micronized solid is from about 0.5 μm to about 500 μm. In some embodiments, the average diameter of particles in a micronized solid is from about 1 μm to about 200 μm. In some embodiments, the average diameter of particles in a micronized solid is from about 2 μm to about 100 μm. In some embodiments, the average diameter of particles in a micronized solid is from about 3 μm to about 50 μm. In some embodiments, a particulate micronized solid comprises particle sizes of less than about 5 microns, less than about 20 microns and/or less than about 100 microns. In some embodiments, the use of particulates (e.g., micronized particles) of ciprofloxacin allows for extended and/or sustained release of ciprofloxacin from any formulation described herein compared to a formulation comprising non-multiparticulate ciprofloxacin. In some instances, formulations containing multiparticulate (e.g. micronized) ciprofloxacin are ejected from a 1 mL syringe adapted with a 27G needle without any plugging or clogging.

In some instances, any particle in any formulation described herein is a coated particle (e.g., a coated micronized particle, nano-particle) and/or a microsphere and/or a liposomal particle. Particle size reduction techniques include, by way of example, grinding, milling (e.g., air-attrition milling (jet milling), ball milling), coacervation, complex coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments formulations described herein comprise crystalline particles and/or isotropic particles. In some embodiments, formulations described herein comprise amorphous particles and/or anisotropic particles. In some embodiments, formulations described herein comprise therapeutic agent particles wherein the therapeutic agent is a free base, or a salt, or a prodrug of a therapeutic agent, or any combination thereof.

The multiparticulates and/or micronized ciprofloxacin formulations described herein are delivered to an auris structure (e.g., middle ear) by means of any type of matrix including solid, liquid or gel matrices. In some embodiments, the multiparticulates and/or micronized ciprofloxacin described herein are delivered to an auris structure (e.g., middle ear) by means of any type of matrix including solid, liquid or gel matrices via intratympanic injection.

Therapeutic Use of Otic Ciprofloxacin Formulations

Anatomy of the Ear

Figure 4:
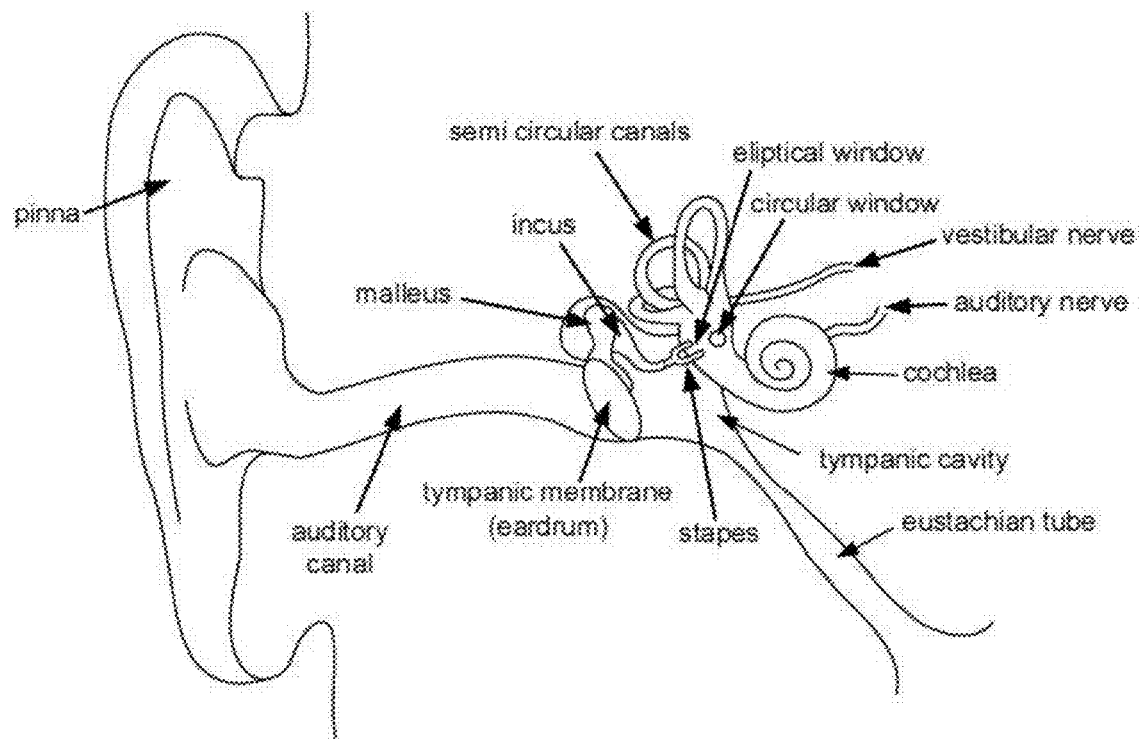
FIG. 4 illustrates the anatomy of the ear.

As shown in FIG. 4, the outer ear is the external portion of the organ and is composed of the pinna (auricle), the auditory canal (external auditory meatus) and the outward facing portion of the tympanic membrane, also known as the ear drum. The pinna, which is the fleshy part of the external ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but which is also accessible within the tympanic cavity, opens into the cochlea of the auris interna. The round window is covered by round window membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window (round window membrane) is correspondingly pushed out and away from the cochlear fluid. This movement of the round window allows movement of fluid within the cochlea, which leads in turn to movement of the cochlear inner hair cells, allowing hearing signals to be transduced. Stiffness and rigidity in round window membrane leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled auris interna, or inner ear, consists of two major components: the cochlear and the vestibular apparatus. The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space can be detected by the movement of the fluid and subsequent signal processing by the sensory organs of the semi-circular canals, called the crista ampullaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The cochlea is the portion of the auris interna related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/scala tympani, which in turn causes the round window membrane to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the organ of Corti moves along with it. The hair cell receptors in the Organ of Corti then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

Otic Disorders or Conditions

Otitis externa (OE), also referred to as swimmer's ear, is an inflammation of the external ear and/or ear canal. OE is primarily caused by bacteria (e.g., *Pseudomonas aeruginosa* and *Staphylococcus aureus*) or fungi (e.g., *Candida albicans* and *Aspergillus*) in the outer ear, which establish infection following damage to the skin of the ear canal. Symptoms of OE include otalgia, swelling, and otorrhea. If the condition progresses significantly, OE may cause temporary conductive hearing loss as a result of the swelling and discharge. Treatment of OE involves eliminating the aggravating pathogen from the ear canal and reducing inflammation, which is usually accomplished by administering combinations of antimicrobial agents, e.g., ciprofloxacin, with anti-inflammatory agents, e.g., steroids.

Otitis media (OM) is an inflammation of the middle ear. Bacterial infection accounts for a large percentage of OM cases, with more than 40% of cases attributed to *Streptococcus pneumoniae* infection. However, viruses, as well as other microbes, may account for OM conditions. Because OM can be caused by a virus, bacteria or both, ciprofloxacin is used to eliminate the underlying pathogen.

Syphilis is a venereal disease, caused by the spirochete *Treponema pallidum*, which may result in otic disorders, particularly cochleovestibular disorders, due to membranous labyrinthitis, and secondarily meningitis. Both acquired and congenital syphilis can cause otic disorders. Symptoms of cochleovestibular disorders resulting from syphilis are often similar to those of other otic disorders, such as AIED and Meniere's disease, and include tinnitus, deafness, vertigo, malaise, sore throat, headaches, and skin rashes.

Treatment of otosyphilis (syphilis presenting otic symptoms) typically includes a combination of steroids and antibacterial agents. Such treatments may be effective in eradicating the spirochete organism while reducing inflammation. However, Treponemas may remain in the cochlear and vestibular endolymph even after eradication from other sites in the body. Accordingly, long term treatment with penicillins may be required to achieve complete eradication of the spirochete organism from the endolymph fluid.

Systemic antimicrobial administration for the treatment of otic disorders, e.g., OE, OM and otosyphilis, may create a potential inequality in drug concentration with higher circulating levels in the serum, and lower levels in the target auris organ structures. As a result, fairly large amounts of drug are required to overcome this inequality in order to deliver sufficient, therapeutically effective quantities to the ear. Further, bioavailability is often decreased due to metabolism of the drug by the liver. In addition, systemic drug administration may increase the likelihood of systemic toxicities and adverse side effects as a result of the high serum amounts required to effectuate sufficient local delivery to the target site. Systemic toxicities may also occur as a result of liver breakdown and processing of the therapeutic agents, forming toxic metabolites that effectively erase any benefit attained from the administered therapeutic.

To overcome the toxic and attendant undesired side effects of systemic delivery of ciprofloxacin (which are generally understood to be toxic to cells), disclosed herein are methods and compositions for local delivery of ciprofloxacin to auris media and/or auris interna structures. In further or alternative embodiments, the auris controlled-release formulations are capable of being administered via intratympanic injection. In some embodiments, the auris controlled release formulation is applied via syringe and needle, wherein the needle is inserted through the tympanic membrane and guided to the area of target site in the middle ear.

Because of the localized targeting of the ciprofloxacin formulations and compositions, as well as the biological blood barrier present in the auris structure, the risk of adverse effects will be reduced as a result of treatment with previously characterized toxic or ineffective ciprofloxacin. Localized administration of antimicrobial agent compositions reduces the risk of development of resistance to antibiotics compared to the risk for development of antibiotic resistance when an antibiotic is administered systemically. The compositions described herein are effective for recurring otic diseases or conditions including, for example, recurring ear infections in children without the need for changing treatment regimens (e.g., in response to development of antibiotic resistance). Accordingly, also contemplated within the scope of the embodiments herein is the use of ciprofloxacin in the treatment of otic diseases or conditions including otitis externa, otitis media, Ramsay Hunt syndrome, otosyphilis, AIED, Meniere's disease, and vestibular neuronitis, including therapeutic agents that have been previously rejected by practitioners because of adverse effects or ineffectiveness of the ciprofloxacin.

Also included within the embodiments disclosed herein is the use of additional auris media and/or auris interna-acceptable agents in combination with the ciprofloxacin formulations and compositions disclosed herein. When used, such agents assist in the treatment of hearing or equilibrium loss or dysfunction resulting from an autoimmune disorder, including vertigo, tinnitus, hearing loss, balance disorders, infections, inflammatory response or combinations thereof. Accordingly, agents that ameliorate or reduce the effects of vertigo, tinnitus, hearing loss, balance disorders, infections, inflammatory response or combinations thereof are also contemplated to be used in combination with the ciprofloxacin formulations described herein.

In some embodiments, the composition further comprises ciprofloxacin as an immediate release agent wherein the immediate release ciprofloxacin is the same agent as the controlled-release agent, a different antimicrobial agent, an additional therapeutic agent, or a combination thereof. In some embodiments, the composition further comprises an additional therapeutic agent, including an additional antimicrobial agent, an anti-inflammatory agent, a corticosteroid, a cytotoxic agent, an anti-TNF agent, a collagen, a gamma-globulin, an interferon, a platelet activator factor antagonist, a nitric oxide synthase inhibitor, or combinations thereof. In another aspect, the additional therapeutic agent is an immediate release or a controlled release agent.

In some embodiments, the additional therapeutic agent is an immediate release agent. In some embodiments, the additional therapeutic agent is a controlled release agent.

Accordingly, provided herein are controlled release ciprofloxacin formulations and compositions to locally treat auris media and/or auris interna structures, thereby avoiding side effects as a result of systemic administration of ciprofloxacin. The locally applied ciprofloxacin formulations and compositions are compatible with auris media and/or auris interna structures, and are administered either directly to the desired auris media and/or auris interna structure, e.g. the tympanic cavity. By specifically targeting the auris media or auris interna structures, adverse side effects as a result of systemic treatment are avoided. Moreover, by providing a controlled release ciprofloxacin formulation or composition to treat otic disorders, a constant and/or extended source of ciprofloxacin is provided to the individual or patient suffering from an otic disorder, reducing or eliminating the variability of treatment.

Intratympanic injection of therapeutic agents also includes the technique of injecting a therapeutic agent behind the tympanic membrane into the auris media and/or auris interna.

However, intra-tympanic injections create several unrecognized problems not addressed by currently available treatment regimens, such as changing the osmolarity and pH of the perilymph and endolymph, and introducing pathogens and endotoxins that directly or indirectly damage ear structures. One of the reasons the art may not have recognized these problems is that there are no approved intra-tympanic compositions: the middle and inner ear provides sui generis formulation challenges. Thus, compositions developed for other parts of the body have little to no relevance for an intra-tympanic composition.

There is no guidance in the prior art regarding requirements (e.g., level of sterility, pH, osmolarity) for otic formulations that are suitable for administration to humans. There is wide anatomical disparity between the ears of animals across species. A consequence of the inter-species differences in auditory structures is that animal models of ear disease are often unreliable as a tool for testing therapeutics that are being developed for clinical approval.

Provided herein are otic formulations that meet stringent criteria for pH, osmolarity, ionic balance, sterility, endotoxin and/or pyrogen levels. The auris compositions described herein are compatible with the microenvironment of the ear (e.g., the middle ear) and are suitable for administration to humans. In some embodiments, the formulations described herein comprise dyes and aid visualization of the administered compositions obviating the need for invasive procedures (e.g., removal of perilymph) during preclinical and/or clinical development of intratympanic therapeutics.

Provided herein are controlled release ciprofloxacin formulations and compositions to locally treat targeted auris structures, thereby avoiding side effects as a result of systemic administration of the ciprofloxacin formulations and compositions. The locally applied ciprofloxacin formulations and compositions and devices are compatible with the targeted auris structures, and administered either directly to the desired targeted auris structure, e.g. the cochlear region, the tympanic cavity or the external ear. By specifically targeting an auris structure, adverse side effects as a result of systemic treatment are avoided. Moreover, clinical studies have shown the benefit of having long term exposure of drug to the perilymph of the cochlea, for example with improved clinical efficacy of sudden hearing loss when the therapeutic agent is given on multiple occasions. Thus, by providing a controlled release ciprofloxacin formulation or composition to treat otic disorders, a constant, and/or extended source of ciprofloxacin is provided to the individual or patient suffering from an otic disorder, reducing or eliminating variabilities in treatment. Accordingly, one embodiment disclosed herein is to provide a composition that enables ciprofloxacin to be released in therapeutically effective doses either at variable or constant rates such as to ensure a continuous release of the at least one agent. In some embodiments, the ciprofloxacin disclosed herein are administered as an immediate release formulation or composition. In other embodiments, the ciprofloxacin are administered as a sustained release formulation, released either continuously, variably or in a pulsatile manner, or variants thereof. In still other embodiments, ciprofloxacin formulation is administered as both an immediate release and sustained release formulation, released either continuously, variably or in a pulsatile manner, or variants thereof. The release is optionally dependent on environmental or physiological conditions, for example, the external ionic environment (see, e.g. Oros® release system, Johnson & Johnson).

In addition, the ciprofloxacin compositions or formulations or devices included herein also include carriers, adjuvants, such as preserving, stabilizing, wetting or emulsifying agents, solution promoters, salts for regulating the osmotic pressure, and/or buffers. Such carriers, adjuvants, and other excipients will be compatible with the environment in the targeted auris structure(s). Accordingly, specifically contemplated for the compositions and devices described herein are carriers, adjuvants and excipients that lack ototoxicity or are minimally ototoxic in order to allow effective treatment of the otic disorders contemplated herein with minimal side effects in the targeted regions or areas.

Intratympanic injection of compositions or devices creates several additional problems that must also be addressed before the composition or device can be administered. For example, there are many excipients that are ototoxic. While these excipients can be used when formulating an active agent for delivery by another method (e.g., topical), their use should be limited, reduced or eliminated when formulating a delivery device to be administered to the ear due to their ototoxic effects.

By way of non-limiting example, the use of the following commonly used solvents should be limited, reduced or eliminated when formulating agents for administration to the ear: alcohols, propylene glycol, and cyclohexane. Thus, in some embodiments, a device disclosed herein is free or substantially free of alcohols, propylene glycol, and cyclohexane. In some embodiments, a device disclosed herein comprises less than about 50 ppm of each of alcohols, propylene glycol, and cyclohexane. In some embodiments, a device disclosed herein comprises less than about 25 ppm of each of alcohols, propylene glycol, and cyclohexane. In some embodiments, a device disclosed herein comprises less than about 20 ppm of each of alcohols, propylene glycol, and cyclohexane. In some embodiments, a device disclosed herein comprises less than about 10 ppm of each of alcohols, propylene glycol, and cyclohexane. In some embodiments, a device disclosed herein comprises less than about 5 ppm of each of alcohols, propylene glycol, and cyclohexane. In some embodiments, a device disclosed herein comprises less than about 1 ppm of each of alcohols, propylene glycol, and cyclohexane.

Further, by way of non-limiting example, the use of the following commonly utilized preservatives should be limited, reduced or eliminated when formulating agents for administration to the ear: Benzethonium chloride, Benzalkonium chloride, and Thiomersal. Thus, in some embodiments, a device disclosed herein is free or substantially free of benzethonium chloride, benzalkonium chloride, and thiomersal. In some embodiments, a device disclosed herein comprises less than about 50 ppm of each of benzethonium chloride, benzalkonium chloride, and thiomersal. In some embodiments, a device disclosed herein comprises less than about 25 ppm of each of benzethonium chloride, benzalkonium chloride, and thiomersal. In some embodiments, a device disclosed herein comprises less than about 20 ppm of each of benzethonium chloride, benzalkonium chloride, and thiomersal. In some embodiments, a device disclosed herein comprises less than about 10 ppm of each of benzethonium chloride, benzalkonium chloride, and thiomersal. In some embodiments, a device disclosed herein comprises less than about 5 ppm of each of benzethonium chloride, benzalkonium chloride, and thiomersal. In some embodiments, a device disclosed herein comprises less than about 1 ppm of each of benzethonium chloride, benzalkonium chloride, and thiomersal.

Certain antiseptics used to disinfect components of therapeutic preparations (or the devices utilized to administer the preparations) should be limited, reduced or eliminated in otic preparations. For example, acetic acid, iodine, and merbromin are all known to be ototoxic. Additionally, chlorhexidene, a commonly used antiseptic, should be limited, reduced or eliminated to disinfect any component of an otic preparation (including devices used to administer the preparation) as it is highly ototoxic in minute concentrations (e.g., 0.05%). Thus, in some embodiments, a device disclosed herein is free or substantially free of acetic acid, iodine, merbromin, and chlorhexidene. In some embodiments, a device disclosed herein comprises less than about 50 ppm of each of acetic acid, iodine, merbromin, and chlorhexidene. In some embodiments, a device disclosed herein comprises less than about 25 ppm of each of acetic acid, iodine, merbromin, and chlorhexidene. In some embodiments, a device disclosed herein comprises less than about 20 ppm of each of acetic acid, iodine, merbromin, and chlorhexidene. In some embodiments, a device disclosed herein comprises less than about 10 ppm of each of acetic acid, iodine, merbromin, and chlorhexidene. In some embodiments, a device disclosed herein comprises less than about 5 ppm of each of acetic acid, iodine, merbromin, and chlorhexidene. In some embodiments, a device disclosed herein comprises less than about 1 ppm of each of acetic acid, iodine, merbromin, and chlorhexidene.

Further, otic preparations require particularly low concentrations of several potentially-common contaminants that are known to be ototoxic. Other dosage forms, while seeking to limit the contamination attributable to these compounds, do not require the stringent precautions that otic preparations require. For example, the following contaminants should be absent or nearly absent from otic preparations: arsenic, lead, mercury, and tin. Thus, in some embodiments, a device disclosed herein is free or substantially free of arsenic, lead, mercury, and tin. In some embodiments, a device disclosed herein comprises less than about 50 ppm of each of arsenic, lead, mercury, and tin. In some embodiments, a device disclosed herein comprises less than about 25 ppm of each of arsenic, lead, mercury, and tin. In some embodiments, a device disclosed herein comprises less than about 20 ppm of each of arsenic, lead, mercury, and tin. In some embodiments, a device disclosed herein comprises less than about 10 ppm of each of arsenic, lead, mercury, and tin. In some embodiments, a device disclosed herein comprises less than about 5 ppm of each of arsenic, lead, mercury, and tin. In some embodiments, a device disclosed herein comprises less than about 1 ppm of each of arsenic, lead, mercury, and tin.

To prevent ototoxicity, ciprofloxacin compositions or formulations or devices disclosed herein are optionally targeted to distinct regions of the targeted auris structures, including but not limited to the tympanic cavity.

Otic Surgery and Implants

In some embodiments, the pharmaceutical formulations, compositions or devices described herein are used in combination with (e.g., implantation, short-term use, long-term use, or removal of) implants (e.g., cochlear implants). As used herein, implants include auris-interna or auris-media medical devices, examples of which include cochlear implants, hearing sparing devices, hearing-improvement devices, short electrodes, tympanostomy tubes, micro-prostheses or piston-like prostheses; needles; stem cell transplants; drug delivery devices; any cell-based therapeutic; or the like. In some instances, the implants are used in conjunction with a patient experiencing hearing loss. In some instances, the hearing loss is present at birth. In some instances, the hearing loss is associated with conditions such as AIED, bacterial meningitis or the like that lead to osteoneogenesis and/or nerve damage with rapid obliteration of cochlear structures and profound hearing loss.

In some instances, an implant is an immune cell or a stem cell transplant in the ear. In some instances, an implant is a small electronic device that has an external portion placed behind the ear, and a second portion that is surgically placed under the skin that helps provide a sense of sound to a person who is profoundly deaf or severely hard-of-hearing. By way of example, such cochlear medical device implants bypass damaged portions of the ear and directly stimulate the auditory nerve. In some instances cochlear implants are used in single sided deafness. In some instances cochlear implants are used for deafness in both ears.

In some embodiments, administration of ciprofloxacin composition described herein in combination with an otic intervention (e.g., an intratympanic injection, a stapedectomy, a tympanostomy, a medical device implant or a cell-based transplant) delays or prevents collateral damage to auris structures, e.g., irritation, inflammation and/or infection, caused by the external otic intervention (e.g., installation of an external device and/or cells in the ear). In some embodiments, administration of ciprofloxacin composition described herein in combination with an implant allows for a more effective restoration of hearing loss compared to an implant alone.

In some embodiments, administration of ciprofloxacin composition described herein reduces damage to cochlear structures caused by underlying conditions (e.g., bacterial meningitis, autoimmune ear disease (AIED)) allowing for successful cochlear device implantation. In some embodiments, administration of a composition or device described herein, in conjunction with otic surgery, medical device implantation and/or cell transplantation, reduces or prevents cell damage and/or inflammation associated with otic surgery, medical device implantation and/or cell transplantation.

In some embodiments, administration of ciprofloxacin composition described herein (e.g., a composition or device comprising a corticosteriod) in conjunction with a cochlear implant or stem cell transplant has a trophic effect (e.g., promotes healthy growth of cells and/or healing of tissue in the area of an implant or transplant). In some embodiments, a trophic effect is desirable during otic surgery or during intratympanic injection procedures. In some embodiments, a trophic effect is desirable after installation of a medical device or after a cell transplant. In some embodiments, a medical device is coated with a composition described herein prior to implantation in the ear.

In some embodiments, administration of an anti-inflammatory or immunosuppressant composition (e.g., a composition comprising an immunosuppresant such as a corticosteroid) reduces inflammation and/or infections associated with otic surgery, implantation of a medical device or a cell transplant. In some instances, perfusion of a surgical area with ciprofloxacin formulation described herein and/or an anti-inflammatory formulation described herein reduces or eliminates post-surgical and/or post-implantation complications (e.g., inflammation, cell damage, infection, osteoneogenesis or the like). In some instances, perfusion of a surgical area with a formulation described herein reduces post-surgery or post-implantation recuperation time.

In one aspect, the formulations described herein, and modes of administration thereof, are applicable to methods of direct perfusion of the middle ear compartments. Thus, the formulations described herein are useful in combination with otic interventions. In some embodiments, an otic intervention is an implantation procedure (e.g., implantation of a hearing device in the cochlea). In some embodiments, an otic intervention is a surgical procedure including, by way of non-limiting examples, cochleostomy, labyrinthotomy, mastoidectomy, stapedectomy, stapedotomy, tympanostomy, endolymphatic sacculotomy or the like. In some embodiments, the middle ear compartments are perfused with a formulation described herein prior to otic intervention, during otic intervention, or after otic intervention, or a combination thereof.

In some embodiments, when perfusion is carried out in combination with otic intervention, the ciprofloxacin compositions are immediate release compositions (e.g., a composition comprising ciprofloxacin). In some of such embodiments, the immediate release formulations described herein are non-thickened compositions and are substantially free of extended release components (e.g., gelling components such as polyoxyethylene-polyoxypropylene copolymers). In some of such embodiments, the compositions contain less than 5% of the extended release components (e.g., gelling components such as polyoxyethylene-polyoxypropylene triblock copolymers) by weight of the formulation. In some of such embodiments, the compositions contain less than 2% of the extended release components (e.g., gelling components such as polyoxyethylene-polyoxypropylene triblock copolymers) by weight of the formulation. In some of such embodiments, the compositions contain less than 1% of the extended release components (e.g., gelling components such as polyoxyethylene-polyoxypropylene triblock copolymers) by weight of the formulation. In some of such embodiments, a composition described herein that is used for perfusion of a surgical area contains substantially no gelling component and is an immediate release composition.

In certain embodiments, a composition described herein is administered before an otic intervention (e.g., before implantation of a medical device or a cell-based therapeutic). In certain embodiments, a composition described herein is administered during an otic intervention (e.g., during implantation of a medical device or a cell-based therapeutic). In other embodiments, a composition described herein is administered after an otic intervention (e.g., after implantation of a medical device or a cell-based therapeutic). In some of such embodiments, a composition described herein that is administered after the otic intervention is an intermediate release or extended release composition (e.g., a composition comprising an antibiotic, a composition comprising an anti-inflammatory agent, a composition comprising a an antibiotic and an anti-inflammatory agent or the like) and contains gelling components as described herein. In some embodiments, an implant (e.g., a tympanostomy tube) is coated with a composition or device described herein prior to insertion in the ear.

Dosing Methods and Schedules

Drugs delivered to the middle or inner ear have been administered systemically via oral, intravenous or intramuscular routes. However, systemic administration for pathologies local to the middle or inner ear increases the likelihood of systemic toxicities and adverse side effects and creates a non-productive distribution of drug in which high levels of drug are found in the serum and correspondingly lower levels are found at the middle or inner ear.

Intratympanic injection of therapeutic agents is the technique of injecting a therapeutic agent behind the tympanic membrane into the middle and/or inner ear. In one embodiment, the formulations described herein are administered directly into the tympanic cavity via transtympanic injection. In another embodiment, the auris-acceptable ciprofloxacin formulations described herein are administered onto the tympanic cavity via a non-transtympanic approach to the middle or inner ear.

In one embodiment the delivery system is a syringe and needle apparatus that is capable of piercing the tympanic membrane and directly accessing the tympanic cavity. In some embodiments, the needle on the syringe is wider than an 18 gauge needle. In another embodiment, the needle gauge is from 18 gauge to 31 gauge. In a further embodiment, the needle gauge is from 25 gauge to 30 gauge. Depending upon the thickness or viscosity of the ciprofloxacin compositions or formulations, the gauge level of the syringe or hypodermic needle may be varied accordingly. In another embodiment, the internal diameter of the needle can be increased by reducing the wall thickness of the needle (commonly referred as thin wall or extra thin wall needles) to reduce the possibility of needle clogging while maintaining an adequate needle gauge.

In another embodiment, the needle is a hypodermic needle used for instant delivery of the gel formulation. The hypodermic needle may be a single use needle or a disposable needle. In some embodiments, a syringe may be used for delivery of the pharmaceutically acceptable gel-based ciprofloxacin-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized. In yet a further embodiment, the sterilization occurs through an autoclave. In another embodiment, the syringe comprises a cylindrical syringe body wherein the gel formulation is stored before use. In other embodiments, the syringe comprises a cylindrical syringe body wherein the pharmaceutically acceptable gel-based ciprofloxacin compositions as disclosed herein is stored before use which conveniently allows for mixing with a suitable pharmaceutically acceptable buffer. In other embodiments, the syringe may contain other excipients, stabilizers, suspending agents, diluents or a combination thereof to stabilize or otherwise stably store the ciprofloxacin or other pharmaceutical compounds contained therein.

In some embodiments, the syringe comprises a cylindrical syringe body wherein the body is compartmentalized in that each compartment is able to store at least one component of the auris-acceptable ciprofloxacin gel formulation. In a further embodiment, the syringe having a compartmentalized body allows for mixing of the components prior to injection into the auris media or auris interna. In other embodiments, the delivery system comprises multiple syringes, each syringe of the multiple syringes contains at least one component of the gel formulation such that each component is pre-mixed prior to injection or is mixed subsequent to injection. In a further embodiment, the syringes disclosed herein comprise at least one reservoir wherein the at least one reservoir comprises ciprofloxacin, or a pharmaceutically acceptable buffer, or a viscosity enhancing agent, such as a gelling agent or a combination thereof. Commercially available injection devices are optionally employed in their simplest form as ready-to-use plastic syringes with a syringe barrel, needle assembly with a needle, plunger with a plunger rod, and holding flange, to perform an intratympanic injection.

In some embodiments, the delivery device is an apparatus designed for administration of therapeutic agents to the middle and/or inner ear. By way of example only: GYRUS Medical Gmbh offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver therapeutic agents to the inner ear. U.S. Patent Application Publication 2007/0167918, which is incorporated herein by reference for such disclosure, further describes a combined otic aspirator and medication dispenser for intratympanic fluid sampling and medicament application.

The auris-acceptable compositions or formulations containing ciprofloxacin described herein are administered for prophylactic and/or therapeutic treatments. In therapeutic applications, the ciprofloxacin compositions are administered to a patient already suffering from an autoimmune disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

Frequency of Administration

In some embodiments, a composition disclosed herein is administered to an individual in need thereof once. In some embodiments, a composition disclosed herein is administered to an individual in need thereof more than once. In some embodiments, a first administration of a composition disclosed herein is followed by a second administration of a composition disclosed herein. In some embodiments, a first administration of a composition disclosed herein is followed by a second and third administration of a composition disclosed herein. In some embodiments, a first administration of a composition disclosed herein is followed by a second, third, and fourth administration of a composition disclosed herein. In some embodiments, a first administration of a composition disclosed herein is followed by a second, third, fourth, and fifth administration of a composition disclosed herein. In some embodiments, a first administration of a composition disclosed herein is followed by a drug holiday.

The number of times a composition is administered to an individual in need thereof depends on the discretion of a medical professional, the disorder, the severity of the disorder, and the individual's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of ciprofloxacin may be administered chronically, that is, for an extended period of time, including throughout the duration of the patient's life in order to ameliorate or otherwise control or limit the symptoms of the patient's disease or condition.

In the case wherein the patient's condition does not improve, upon the doctor's discretion the administration of ciprofloxacin may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of ciprofloxacin may be given continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's otic conditions has occurred, a maintenance ciprofloxacin dose is administered if necessary. Subsequently, the dosage or the frequency of administration, or both, is optionally reduced, as a function of the symptoms, to a level at which the improved disease, disorder or condition is retained. In certain embodiments, patients require intermittent treatment on a long-term basis upon any recurrence of symptoms.

The amount of ciprofloxacin that will correspond to such an amount will vary depending upon factors such as the particular compound, disease condition and its severity, according to the particular circumstances surrounding the case, including, e.g., the route of administration, the auto-immune condition being treated, the target area being treated, and the subject or host being treated. In general, however, doses employed for adult human treatment will typically be in the range of 0.02-50 mg per administration, preferably 1-15 mg per administration. The desired dose is presented in a single dose or as divided doses administered simultaneously (or over a short period of time) or at appropriate intervals.

Pharmacokinetics of Otic Formulations

In one embodiment, the formulations disclosed herein additionally provides an immediate release of ciprofloxacin from the composition, or within 1 minute, or within 5 minutes, or within 10 minutes, or within 15 minutes, or within 30 minutes, or within 60 minutes or within 90 minutes. In other embodiments, a therapeutically effective amount of ciprofloxacin is released from the composition immediately, or within 1 minute, or within 5 minutes, or within 10 minutes, or within 15 minutes, or within 30 minutes, or within 60 minutes or within 90 minutes. In certain embodiments the composition comprises an auris-pharmaceutically acceptable gel formulation providing immediate release of ciprofloxacin. Additional embodiments of the formulation may also include an agent that enhances the viscosity of the formulations included herein.

In other or further embodiments, the formulation provides an extended release formulation ciprofloxacin. In certain embodiments, diffusion of ciprofloxacin from the formulation occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of ciprofloxacin is released from the formulation for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In other embodiments, the formulation provides both an immediate release and an extended release formulation of ciprofloxacin. In yet other embodiments, the formulation contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations. In a further embodiment the formulation provides an immediate release of a first ciprofloxacin and an extended release of a second ciprofloxacin or other therapeutic agent. In yet other embodiments, the formulation provides an immediate release and extended release formulation of ciprofloxacin, and at least one therapeutic agent. In some embodiments, the formulation provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations of a first ciprofloxacin and second therapeutic agent, respectively.

In a specific embodiment the formulation provides a therapeutically effective amount of ciprofloxacin at the site of disease with essentially no systemic exposure. In an additional embodiment the formulation provides a therapeutically effective amount of ciprofloxacin at the site of disease with essentially no detectable systemic exposure. In other embodiments, the formulation provides a therapeutically effective amount of ciprofloxacin at the site of disease with little or no detectable systemic exposure.

The combination of immediate release, delayed release and/or extended release ciprofloxacin compositions or formulations may be combined with other pharmaceutical agents, as well as the excipients, diluents, stabilizers, tonicity agents and other components disclosed herein. As such, depending upon the thickness or viscosity desired, or the mode of delivery chosen, alternative aspects of the embodiments disclosed herein are combined with the immediate release, delayed release and/or extended release embodiments accordingly.

In certain embodiments, the pharmacokinetics of the ciprofloxacin formulations described herein are determined by intratympanic injection of the formulation into the test animal (including by way of example, a guinea pig or a chinchilla). At a determined period of time (e.g., 6 hours, 12 hours, 1 day, 2 days, 3 days, 4 days, 5 days, 6 days, and 7 days for testing the pharmacokinetics of a formulation over a 1 week period), the test animal is euthanized and the level of ciprofloxacin in the ear is measured. In addition, the systemic level of ciprofloxacin is measured by withdrawing a blood sample from the test animal. In order to determine whether the formulation impedes hearing, the hearing of the test animal is optionally tested.

Figure 5:
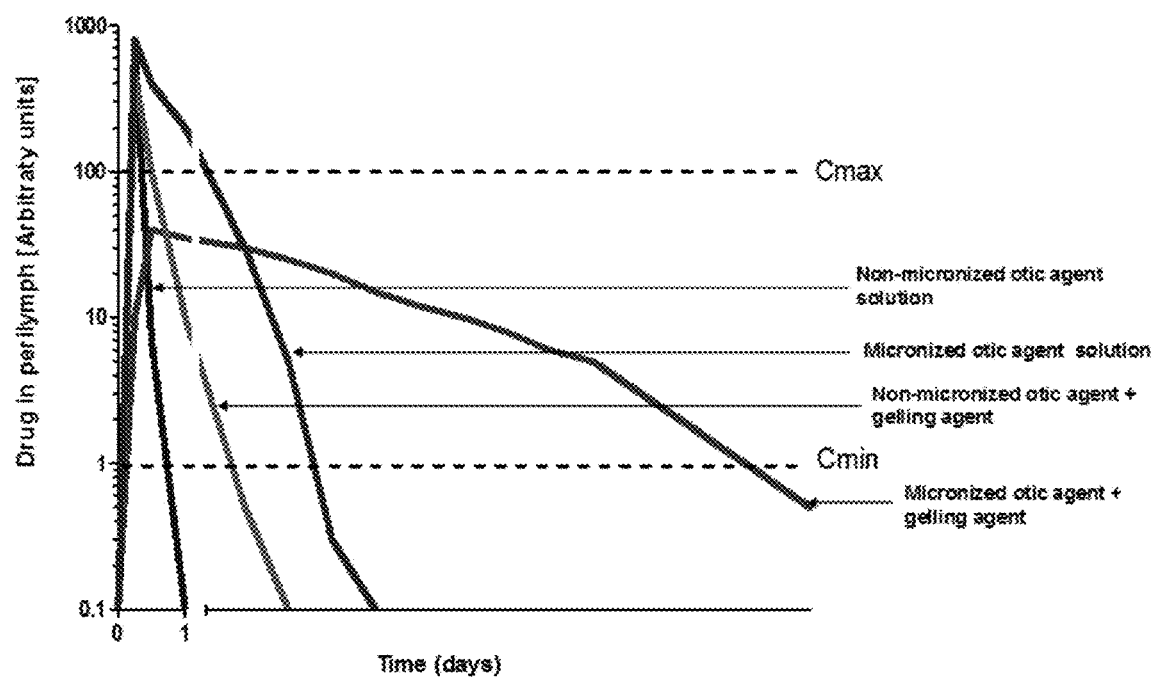
FIG. 5 schematically illustrates sustained release of ciprofloxacin from an otic formulation formed according to the method disclosure herein.

FIG. 5 shows predicted tunable release of an active agent from four compositions.

Kits/Articles of Manufacture

The disclosure also provides kits for preventing, treating or ameliorating the symptoms of a disease or disorder in a mammal. Such kits generally will comprise one or more of controlled-release ciprofloxacin compositions or devices disclosed herein, and instructions for using the kit. The disclosure also contemplates the use of one or more of controlled-release ciprofloxacin compositions, in the manufacture of medicaments for treating, abating, reducing, or ameliorating the symptoms of a disease, dysfunction, or disorder in a mammal, such as a human that has, is suspected of having, or at risk for developing an ear disorder.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of ciprofloxacin formulations compositions provided herein are contemplated as are a variety of treatments for any disease, disorder, or condition that would benefit by controlled release administration of ciprofloxacin to the ear.

In some embodiments, a kit includes one or more additional containers, each with one or more of various materials (such as reagents, optionally in concentrated form, and/or devices) desirable from a commercial and user standpoint for use of a formulation described herein. Non-limiting examples of such materials include, but are not limited to, buffers, diluents, filters, needles, syringes; carrier, package, container, vial and/or tube labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example 1—Form (Anhydrous/Hydrate) of Ciprofloxacin—Loss on Drying

To assess the form of ciprofloxacin samples described in the present disclosure, a comparison experiment is conducted to evaluate the sample's loss of weight upon heating. Loss of less than 2% in weight generally indicates that the sample is in anhydrous form. On the other hand, loss of more than 10% in weight generally indicates that the sample is in hydrate form. The conditions and results of the experiment are summarized below:

Experimental Setup—Loss on Drying:
  If suspension: Pipette cipro suspension onto filter on vacuum filter flask
  Transfer filter/dry powder to 40° C. oven, hold 24 hours
  Transfer solid to pre-weighed aluminum pan and weigh solid
  Transfer pan to 125° C. oven, hold one hour
  Weigh again and determine weight loss due to 125° C.

TABLE 1

Form (Anhydrous/Hydrate) of Ciprofloxacin - Loss on Drying

| Sample No. | Sample Description | Weight Loss on Drying |
|---|---|---|
| 1 | Cipro anhydrous (dry powder; no suspension) | 0.1% |
| 2 | Cipro hydrate (dry powder; no suspension) | 11.1% |
| 3 | Cipro suspension (5° C. addition of Cipro anhydrous powder to water, homogenized) | 13.7% |
| 4 | Cipro suspension (135° C. autoclave of Sample 3; hot suspension) | 1.0% |
| 5 | Cipro suspension (135° C. autoclave of Sample 3; cooled down suspension) | 15.9% |

The first entry indicates that ciprofloxacin anhydrous losses less than 1% weigh upon oven heating. The second entry indicates that ciprofloxacin hydrate losses more than 10% weigh upon oven heating. The third entry indicates that ciprofloxacin anhydrous is converted into hydrate form upon mixing with water (as the solid isolated from the mixture losses more than 10% weigh upon oven hearing). The fourth entry indicates that that the ciprofloxacin hydrate suspension in third entry, upon heating at high temperature, reverts back to anhydrous form in the hot suspension. Finally, the last entry indicates that ciprofloxacin in the hot suspension heated at high temperature is re-hydrated during cool-down. Without wishing to be bound by any particular theory, it is contemplated that the hydrate-anhydrous-hydrate transformation contributes to the solidification of the ciprofloxacin suspension described herein.

Example 2—Form (Anhydrous/Hydrate) of Ciprofloxacin—X-Ray Characterization

Figure 2:
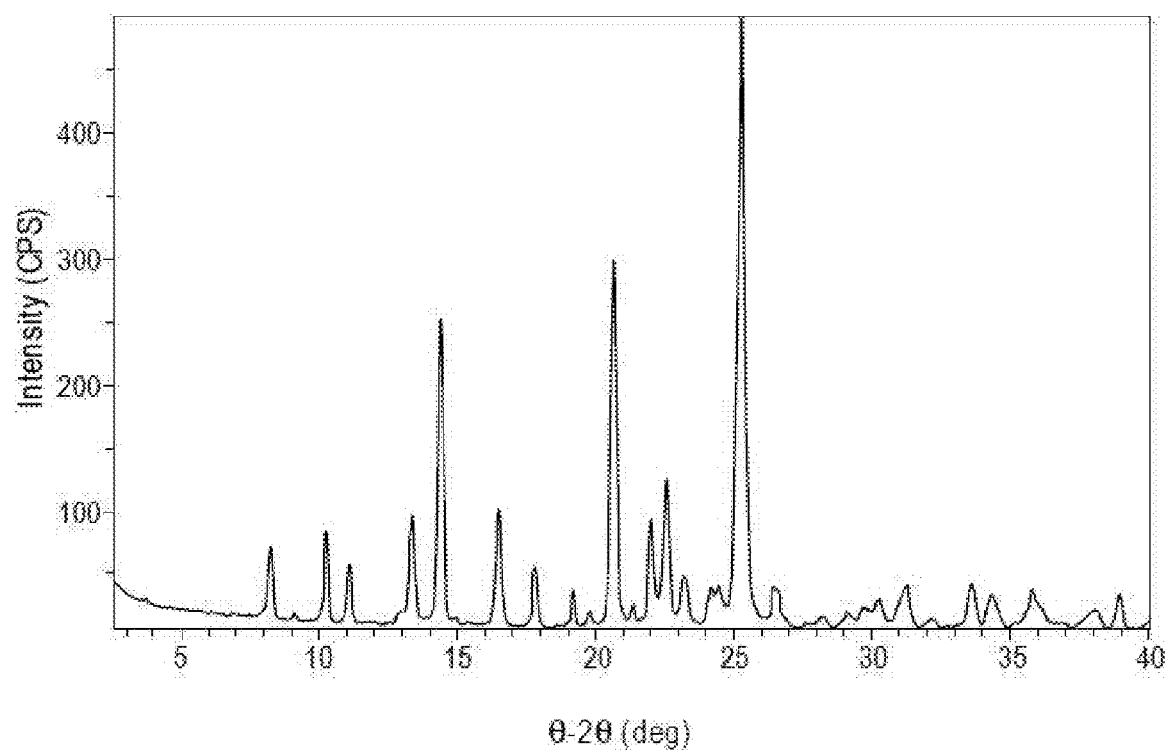
FIG. 2 shows X-ray characterization of an aqueous ciprofloxacin suspension after heat sterilization at 135° C. (without cooling down)

FIG. 1 shows X-ray characterization of ciprofloxacin anhydrous (bottom), ciprofloxacin hydrate (middle), and an aqueous ciprofloxacin suspension formed according to the method disclosure herein (top). FIG. 2 shows X-ray characterization of an aqueous ciprofloxacin suspension after heat sterilization at 135° C. (without cooling down). In a non-limiting sterilization example, dry powder ciprofloxacin free base anhydrate with the X-ray characterization at the bottom of FIG. 1 is used. When this is added to water, it immediately hydrates. Notably, ciprofloxacin changes forms (showing increasing particle size and visually showing long needles forming) and thickens (and can solidify) during this step. This could be similar to the solidification during cool-down, suggesting that the conversion from anhydrate at high temperature back to hydrate at low temperature is involved in causing the solidification.

Referring now to FIG. 1, the X-ray characterization at the bottom represents ciprofloxacin anhydrous, and the X-ray characterization in the middle represents ciprofloxacin hydrate. Referring now to FIG. 2, the X-ray characterization represents an aqueous ciprofloxacin suspension after heat sterilization at 135° C. (without cooling down). Comparison of the X-ray characterization of those non-limiting examples indicates the presence of ciprofloxacin in anhydrous form when an aqueous ciprofloxacin suspension is heated at high temperature (e.g. 135° C.)

When this hot ciprofloxacin free base (anhydrous) suspension is cooled down, it solidified. This solidified material is shown to be the hydrate form.

Referring again to FIG. 1, the X-ray characterization at the bottom represents ciprofloxacin anhydrous, and the X-ray characterization in the middle represents ciprofloxacin hydrate. The X-ray characterization at the top represents an aqueous ciprofloxacin suspension after heat sterilization at the lower temperature exposure (e.g. 100° C.-120° C.) after cooling down. Comparison of the X-ray characterization of those non-limiting examples indicates the presence of ciprofloxacin in hydrate form when an aqueous ciprofloxacin suspension is heated at the lower temperature exposure (e.g. 100° C.-120° C.) after cooling down.

Example 3—Heat Sterilization of Ciprofloxacin

To demonstrate the features of the sterilization process described herein, three manufacturing experiments are conducted by Alliance Medical Products (9342 Jeronimo Rd, Irvine, Calif. 92618), with results summarized below.

Engineering (Process Development) Manufacturing Run, Protocol 14047: 105° C. exposure for 2 hours; no solidification of ciprofloxacin suspension.

Engineering (Process Development) Manufacturing Run, Protocol 14047 addendum 1: 115° C. exposure for 1 hour; no solidification of ciprofloxacin suspension.

Engineering (Process Development) Manufacturing Run, Protocol 13156: >121.5° C. exposure for 20 minutes; ciprofloxacin suspension solidified.

Changes in the form during manufacturing process also results in changes in the particle size of ciprofloxacin API. Ciprofloxacin free base anhydrous API powder has a typical particle size of D90 under 15 µm, upon conversion to the hydrate form, particle size increases to D90 of around 60 µm. The final drug product has particle size of D90 of about 25 µm. Without wishing to be bound by any particular theory, one or more features of the sterilization method described herein, including but not limited to the use of a lower sterilization temperature and/or homogenization of the suspension during the sterilization process, would contribute to the particle size distribution of ciprofloxacin in the suspension, and in the final product. In some embodiments, it is the use of a lower sterilization temperature and homogenization of the suspension during the sterilization process that contributes to the particle size distribution of ciprofloxacin in the suspension, and in the final product.

Example 4—Filtration Sterilization of a Diluent Composition

The heat sterilized ciprofloxacin suspension could be further processed into a ready-to-use drug product, such as by mixing with a diluent composition. In this example, the diluent composition is an aqueous solution of a polyoxyethylene-polyoxypropylene copolymer (e.g. poloxamer 407), a buffering agent (tromethamine), an osmolarity adjusting agent (e.g. sodium chloride), and a pH adjusting agent (hydrochloric acid) prepared as follows.

A concentrated poloxamer 407 buffered solution is prepared by mixing and dissolving all components with nitrogen sparging, under pressure, at approximately 2-7° C. The poloxamer 407 buffered diluents composition is sterile filtered through a 0.22 µm filter for further combination with the ciprofloxacin suspension.

Example 5—Determination of Manufacturing Conditions for Sterile Filtration

The temperature of the room is maintained below 25° C. to retain the temperature of the solution at below 19° C. The temperature of the solution is maintained at below 19° C. up to 3 hours of the initiation of the manufacturing, without the need to chill/cool the container.

Three different Sartoscale (Sartorius Stedim) filters with a surface area of 17.3 cm$^2$ are evaluated at 20 psi and 14° C. of solution 1) Sartopore 2, 0.2 µm 5445307HS-FF (PES), flow rate of 16 mL/min 2) Sartobran P, 0.2 µm 5235307HS-FF (cellulose ester), flow rate of 12 mL/min 3) Sartopore 2 XLI, 0.2 µm 5445307IS-FF (PES), flow rate of 15 mL/min Sartopore 2 filter 5441307H4-SS is used, filtration is carried out at the solution temperature using a 0.45, 0.2 µm Sartopore 2 150 sterile capsule (Sartorius Stedim) with a surface area of 0.015 m$^2$ at a pressure of 16 psi. Flow rate is measured at approximately 100 mL/min at 16 psi, with no change in flow rate while the temperature is maintained in the 6.5-14° C. range. Decreasing pressure and increasing temperature of the solution causes a decrease in flow rate due to an increase in the viscosity of the solution. Discoloration of the solution is monitored during the process.

TABLE 2

Predicted filtration time for a 17% poloxamer 407 diluent composition at a solution temperature range of 6.5-14° C. using Sartopore 2, 0.2 µm filters at a pressure of 16 psi of pressure

| Filter | Size (m$^2$) | Estimated flow rate (mL/min) | Time to filter 8 L (estimated) |
|---|---|---|---|
| Sartopore 2, size 4 | 0.015 | 100 mL/min | 80 min |
| Sartopore 2, size 7 | 0.05 | 330 mL/min | 24 min |
| Sartopore 2, size 8 | 0.1 | 670 mL/min | 12 min |

Viscosity, Tgel and UV/Vis absorption is checked before filtration evaluation. UV/Vis spectra are obtained by an Evolution 160 UV/Vis (Thermo Scientific). A peak in the range of 250-300 nm is attributed to BHT stabilizer present in the raw material (poloxamer). Table 3 lists physicochemical properties of the above solutions before and after filtration.

TABLE 3

Physicochemical properties of 17% poloxamer 407 diluent composition before and after filtration

| Sample | Tgel (° C.) | Viscosity$^a$ @ 19° C. (cP) | Absorbance @ 274 nm |
|---|---|---|---|
| Before filtration | 22 | 100 | 0.3181 |
| After filtration | 22 | 100 | 0.3081 |

$^a$Viscosity measured at a shear rate of 37.5 s$^{-1}$

The above process is applicable for manufacture of 17% P407 formulations, and includes temperature analysis of the room conditions. Preferably, a maximum temperature of 19° C. reduces cost of cooling the container during manufacturing. In some instances, a jacketed container is used to further control the temperature of the solution to ease manufacturing concerns.

Example 6—Preparation of a Ready-to-Use Ciprofloxacin Poloxamer Formulation

In this non-limiting example, a ciprofloxacin suspension prepared as in Example 3 and a poloxamer 407 diluent are mixed together at aseptic conditions to form a ready-to-use otic formulation that meets the high sterility requirements for intratympanic administered composition. An exemplary formulation is provided below as a thermoreversible gel that is an injectable liquid at room temperature and gels in the ear after intratympanic delivery.

| Ingredient | Quality Standard | Function | Composition (mg/mL)[a] | Composition (mg/vial)[b] |
|---|---|---|---|---|
| Ciprofloxacin | USP | Active ingredient | 60 | 210 |
| Poloxamer 407 | NF | Gel formation | 157 | 549.5 |
| Sodium Chloride | USP | Osmolality modifier | 4.5 | 15.75 |
| Tromethamine | USP | Buffering agent | 5.8 | 20.3 |
| Hydrochloric Acid (37.5% w/w) | NF | pH adjustment | QS for pH adjustment (pH 7.0-8.0) | QS for pH adjustment (pH 7.0-8.0) |
| Water for Injection (WFI) | USP | Vehicle | QS to 1040 | QS to 3640 |

[a]Density of OTO-201 Drug Product containing 60 mg/mL ciprofloxacin USP has been determined to be 1.04 g/mL.
[b]Fill volume is approximately 3.5 mL per vial.

The formulation has less than about 50 colony forming units (cfu) of microbiological agents per gram of formulation, and has less than about 5 endotoxin units (EU) per kg of body weight of a subject. The composition is suitable for intratympanic administration.

Example 7—Preparation of a Ready-to-Use Vial Containing Ciprofloxacin Poloxamer Formulation The formulation in Example 6 is filled into an aseptic container (e.g. a vial), stoppered, and capped, all under aseptic process conditions to form a ready-to-use medical/pharmaceutical product that meets the sterility requires for intratympanic administration. The formulation in the vial has less than about 50 colony forming units (cfu) of microbiological agents per gram of formulation, and has less than about 5 endotoxin units (EU) per kg of body weight of a subject.

Example 8—In Vivo Testing of Intratympanic Injection of Ciprofloxacin Formulation in a Guinea Pig A cohort of 21 guinea pigs (Charles River, females weighing 200-300 g) is intratympanically injected with 50 μL of different P407-ciprofloxacin formulation prepared in Example 6 or Example 7. Animals are dosed on day 1. The release profile for the formulations is determined based on analysis of the perilymph.

While preferred embodiments of the present invention have been shown and described herein, such embodiments are provided by way of example only. Various alternatives to the embodiments described herein are optionally employed in practicing the inventions. It is intended that the following claims define the scope of the invention and that methods and structures within the scope of these claims and their equivalents be covered thereby.

We claim:
1. A method of making a sterilized ciprofloxacin composition, comprising the steps of:
  (a) heating an aqueous suspension comprising ciprofloxacin particles essentially in the form of ciprofloxacin hydrate particles at a temperature ranging from about 100° C. to about 120° C.; and
  (b) combining the aqueous suspension comprising ciprofloxacin particles with a sterilized aqueous solution comprising a thermoreversible polymer to form an otic formulation.
2. The method of claim 1, wherein the aqueous suspension in step (a) is essentially free of organic solvent.
3. The method of claim 1, wherein the ciprofloxacin particles in step (a) are present in the aqueous suspension at a concentration of from about 4 wt % to about 30 wt %.
4. The method of claim 1, wherein the ciprofloxacin particles in step (a) are present in the aqueous suspension at a concentration of from about 10 wt % to about 16 wt %.
5. The method of claim 1, wherein the ciprofloxacin particles in step (b) are homogenized in the aqueous suspension.
6. The method of claim 1, wherein the ciprofloxacin particles in step (b) have a D90 of from about 5 μm to about 40 μm after cooling down.
7. The method of claim 1, wherein the thermoreversible polymer in step (b) is poloxamer 407.
8. The method of claim 1, wherein the aqueous solution in step (b) further comprises a buffer agent.
9. The method of claim 1, wherein the aqueous solution in step (b) further comprises an osmolarity modifier.
10. The method of claim 1, wherein the aqueous solution in step (b) is sterilized through filtration sterilization, heat sterilization, or radiation sterilization.
11. The method of claim 1, wherein the aqueous solution in step (b) is sterilized through filtration sterilization.
12. The method of claim 1, wherein the aqueous suspension and the aqueous solution are combined under aseptic condition.
13. The method of claim 1, wherein the otic formulation comprises from about 5.5 wt % to about 6.5 wt % of ciprofloxacin.
14. The method of claim 1, wherein the otic formulation comprises from about 15 wt % to about 17 wt % of the thermoreversible polymer, and wherein the thermoreversible polymer is poloxamer 407.
15. The method of claim 1, where the otic formulation has a pH of from about 7.0 to about 8.0.
16. The method of claim 1, where the otic formulation has an osmolarity of from about 270 mOsm/L to about 320 mOsm/L.
17. A sterilized otic formulation formed by the method of claim 1, the sterilized otic formulation comprising: from about 5.5 wt % to about 6.5 wt % multiparticulate ciprofloxacin; from about 15 wt % to about 17 wt % poloxamer 407; and water, wherein the composition has a pH of from about 7.0 to about 8.0, an osmolarity of from about 270 to about 320 mOsm/L, and wherein the sterilized otic formulation provides sustained release of a therapeutically effective amount of ciprofloxacin into the ear for a period of at least 5 days after a single administration.

18. The sterilized otic formulation of claim 17, wherein the multiparticulate ciprofloxacin has a D90 of from about 5 μm to about 40 μm.

19. The sterilized otic formulation of claim 17, wherein the ciprofloxacin particles are homogenized in the sterilized otic formulation.

20. A ready-to-use otic product, comprising an aseptic vial and the sterilized otic formulation of claim 17.

* * * * *